United States Patent
Hoyer et al.

(10) Patent No.: US 11,896,577 B2
(45) Date of Patent: Feb. 13, 2024

(54) SHORT-ACTING PSYCHOACTIVE COMPOUNDS OF THE MDMA CLASS

(71) Applicant: Mydecine Innovations Group Inc., Denver, CO (US)

(72) Inventors: Denton W. Hoyer, West Haven, CT (US); Robert F. Roscow, Longmont, CO (US); Rong Ling, Edmonton (CA); Chuanjun Gao, Edmonton (CA)

(73) Assignee: Mydecine Innovations Group Inc., Denver, CO (US)

( * ) Notice: Subject to any disclaimer, the term of this patent is extended or adjusted under 35 U.S.C. 154(b) by 0 days.

(21) Appl. No.: 18/209,334

(22) Filed: Jun. 13, 2023

(65) Prior Publication Data

US 2023/0321034 A1    Oct. 12, 2023

Related U.S. Application Data

(63) Continuation-in-part of application No. PCT/US2022/037193, filed on Jul. 14, 2022.

(60) Provisional application No. 63/322,806, filed on Mar. 23, 2022, provisional application No. 63/221,597, filed on Jul. 14, 2021.

(51) Int. Cl.
| | | |
|---|---|---|
| *A61K 31/39* | (2006.01) | |
| *A61K 31/381* | (2006.01) | |
| *A61K 45/06* | (2006.01) | |

(52) U.S. Cl.
CPC ............ *A61K 31/39* (2013.01); *A61K 31/381* (2013.01); *A61K 45/06* (2013.01)

(58) Field of Classification Search
None
See application file for complete search history.

(56) References Cited

U.S. PATENT DOCUMENTS 9,649,297 B2    5/2017    Bird

FOREIGN PATENT DOCUMENTS

WO    WO-2022010937 A1 *    1/2022    ............ A61P 25/22

OTHER PUBLICATIONS

Mithoefer et al. (JournalofPsychopharmacology. 25(4): 439-452, 2010).*
Wikipedia "Bioisostere" (https://en.wikipedia.org/wiki/Bioisostere-available online as of Sep. 27, 2015).*
Gyllvik,'The Therapeutic Potential of Psilocybin and 3,4-Methylenedioxymethamphetamine in the Treatment of Depression and Post-Traumatic Stress Di_sorder', Bachelor Degree Project in Cognitive Neuroscience, University of Skovde, 2020, pp. 1-37; p. 8, para 2; Figure 1; p. 9, para 4 to p. 10, par? 3; p. 16, para 4 to p. 18, para 2; Table 3; p. 25, para 3.
Pubchem-SID:397275444 Deposit Date: Dec. 6, 2019 (Dec. 6, 2019) pp. 1-5; p. 2.
Pubchem-SID:395983706 Deposit Date: Dec. 6, 2019 (Dec. 6, 2019) pp. 1-5; p. 2.
Pubchem-SID:3.10504045 Deposit Date: Feb. 15, 2016 (Feb. 15, 2016) pp. 1-5; p. 2.
International Search Report and Written Opinion dated Dec. 19, 2022, 12 pages.
Garcia-Garcia et al., 5-HT(1A) receptors in mood and anxiety: recent insights into autoreceptor versus heteroreceptor function. Psychopharmacology (Berl). Feb. 2014;231(4):623-36.
Kirsten C. et al., Serotonin (1A) receptor involvement in acute 3,4-methylenedioxymethamphetamine (MDMA) facilitation of social interaction in the rat. Progress in Neuro-Psychopharmacology and Biological Psychiatry, vol. 29, Issue 5, 2005, pp. 648-657.

* cited by examiner

*Primary Examiner* — Bong-Sook Baek
(74) *Attorney, Agent, or Firm* — Berg Hill Greenleaf Ruscitti LLP

(57)    ABSTRACT

The present invention is directed to novel chemical compositions of matter, and in particular novel MDMA class of compounds having substituted methylenedioxyphenethylamine and substituted amphetamine, having a metabolically labile thioether group.

6 Claims, No Drawings

SHORT-ACTING PSYCHOACTIVE COMPOUNDS OF THE MDMA CLASS

CROSS-REFERENCE TO RELATED APPLICATIONS

This application is a bypass continuation-in-part of International PCT Application No. PCT/US22/37193, filed Jul. 14, 2022, which claims the benefit of and priority to U.S. Provisional Application No. 63/221,597 filed Jul. 14, 2021, and U.S. Provisional Application No. 63/322,806 filed Mar. 23, 2022. The specification, claims, and drawings of which are incorporated herein by reference in their entirety.

TECHNICAL FIELD

The present invention is directed to novel chemical compositions of matter. Specifically, novel analogs of the MDMA class of compounds, and their precursors having unique pharmacokinetic characteristics.

BACKGROUND

Racemic 3,4-methylenedioxymethamphetamine (rac-MDMA), is an important experimental psychoactive drug with potential in the supervised treatment of various psychological disorders, including post-traumatic stress disorder (PTSD) and related psychological trauma among other therapeutic uses. MDMA. Rac-MDMA, also generally referred to herein as MDMA, has two enantiomers, S-MDMA and R-MDMA.

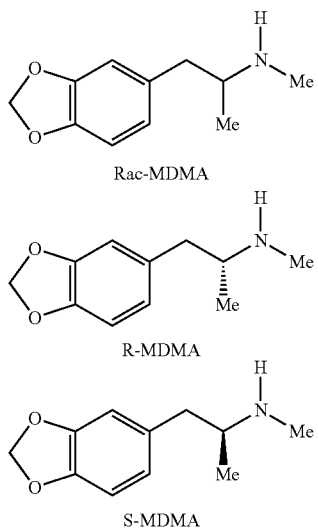

Administration of racemic MDMA is followed by the appearance of at least seven racemic metabolites. At least two of the major metabolites, rac-MDMA and racemic HMMA, are active and have effects which may mirror some aspects of MDMA itself, thus potentially responsible for extending the duration of physiological and psychological effects of the parent drug. Ideally, one would want a new drug whose primary metabolites are devoid of activity and which arise quickly thereby inactivating the drugs and shortening the duration of action.

However, the duration of action of rac-MDMA is not ideal for therapeutic administration, having a duration of action of approximately 4-6 hours. To address these concerns, there exists a need for shorter acting MDMA analogs that still provide the therapeutic benefits of rac-MDMA. Such novel compositions may offer more convenient duration of action after therapeutic dosing in clinical settings.

SUMMARY OF THE INVENTION

In one aspect, the invention includes novel classes of thioether containing analogs of rac-MDMA and the respective R and S forms as short duration of action MDMA replacements. These analogs contain a metabolically labile thioether which mimics the methylenedioxy ring of MDMA itself. Since these changes are conservative and are consistent with the structure-activity requirements of racemic MDMA itself and related analogs, the novel compounds of this new class can be active in their parent forms but not in their oxidized metabolized forms. The speed of inactivation can be rapid, consistent with the nearly universal trend of thioether containing drugs to be rapidly enzymatically oxidized in vivo. In this manner, the novel compounds of the invention can exhibit increased metabolic inactivation, resulting in a decreased duration of action.

Another aspect of the invention includes novel MDMA analog compounds, and in particular the compounds comprising isomers of 2H-1,3-benzoxathiole having replaced the methylenedioxyphenyl structure in MDMA, including both the racemic and R, S enantiomers for each positional isomer as shown below.

Another aspect of the invention, includes novel MDMA analog compounds, and in particular the compounds which comprise benzthiophenes, wherein in this example 1-benzothiophene having replaced the methylenedioxyphenyl structure in MDMA, including both the racemic and R, S enantiomers for each positional isomer as shown below.

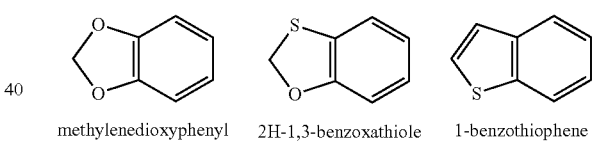

methylenedioxyphenyl    2H-1,3-benzoxathiole    1-benzothiophene

One aspect of the invention may include a novel MDMA analog compound comprising:

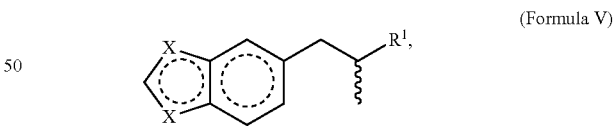

(Formula V)

wherein:
X is S, O, or CH; and
$R^1$ is $NR^2R^3$;
$R^2$ is H or $CH_3$;
$R^3$ is $CH_3$; and
wherein said dashed lines represents possible double bond positions according to the configuration of X being S, O, or CH;
or a pharmaceutically acceptable salt thereof.

Another aspect of the invention may include a novel MDMA analog compound selected from the group consisting of:

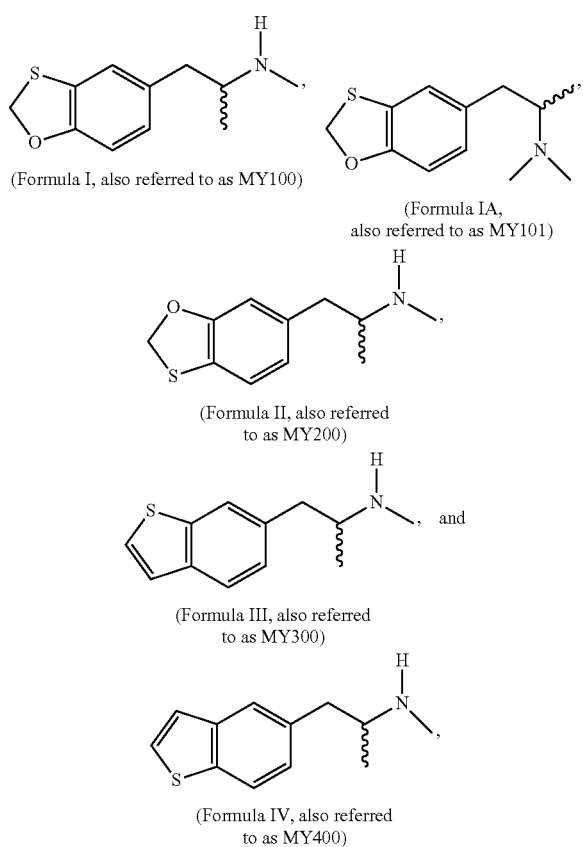

(Formula I, also referred to as MY100)

(Formula IA, also referred to as MY101)

(Formula II, also referred to as MY200)

(Formula III, also referred to as MY300)

(Formula IV, also referred to as MY400)

or a pharmaceutically acceptable salt thereof.

In another aspect, the present invention includes novel MDMA analogs identified herein as the compound according to Formulas I-V, (also referred to as a/the compound(s) or composition(s) of the invention), or a pharmaceutically acceptable salt, solvate, stereoisomer, tautomer, or prodrug thereof as described herein. (Notably, reference to Formula I, independently includes the compounds of Formula I and/or IA).

Additional aspects of the current invention include a compound of Formula I-V, or a pharmaceutically acceptable salt, solvate, stereoisomer, tautomer, or prodrug thereof, for use in recreational, psychological, or medical therapies.

Additional aspects of the present invention provides systems, methods, and compositions for novel MDMA analogs according to the compounds of Formula I-V, and a pharmaceutically acceptable carrier or diluent, which may preferably further include a method of treatment of the human or animal body using one or more of the novel compounds, or pharmaceutical compositions described herein.

Additional aspects of the present invention provide a method for treating a disease or condition, and optionally where the composition of the invention has a decreased duration of action comprising: administering to a subject in need thereof, a therapeutically effective amount of a one or more compounds of the invention according to Formulas I-V, or a pharmaceutical composition containing a therapeutically effective amount of a one or more compounds of the invention according to Formulas I-V and a pharmaceutically carrier.

Another aspect of the invention may include a compound selected from the group consisting of: racemic 1-(2H-1,3-benzoxathiol-5-yl)-N-methylpropan-2-amine; (2R)-1-(2H-1,3-benzoxathiol-5-yl)-N-methylpropan-2-amine; (2S)-1-(2H-1,3-benzoxathiol-5-yl)-N-methylpropan-2-amine; 1-(2H-1,3-benzoxathiol-6-yl)-N-methylpropan-2-amine; (2R)-1-(2H-1,3-benzoxathiol-6-yl)-N-methylpropan-2-amine; (2S)-1-(2H-1,3-benzoxathiol-6-yl)-N-methylpropan-2-amine; 1-(1-benzothiophen-6-yl)-N-methylpropan-2-amine; (2R)-1-(1-benzothiophen-6-yl)-N-methylpropan-2-amine; (2S)-1-(1-benzothiophen-6-yl)-N-methylpropan-2-amine; 1-(1-benzothiophen-5-yl)-N-methylpropan-2-amine; (2R)-1-(1-benzothiophen-5-yl)-N-methylpropan-2-amine; and (2S)-1-(1-benzothiophen-5-yl)-N-methylpropan-2-amine, or a pharmaceutically acceptable salt, solvate, stereoisomer, tautomer, or prodrug thereof, for use in recreational, psychological, or medical therapies.

Additional aspects of the invention include methods of synthesizing the compounds of the invention according to Formulas I-V, which may preferably include a starting ring structure comprising a benzothiazole or benzoxathiole. Additional aspects of the invention include pharmaceutical compositions comprising one or more compounds of the invention according to Formulas I-V.

Additional aspects of the invention may become evident based on the specification and claims presented below.

DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The invention includes novel analogs of Rac-MDMA, that mimic the pharmacokinetic effects of MDMA in a subject but that exhibit a decreased duration of action. In one preferred embodiment, the composition of the invention include the addition of a metabolically labile thioether group which mimics the methylenedioxy ring of MDMA. The sulfur position of the thioether can be oxidized after ingestion by a subject, by an oxygenase or peroxidase enzyme, to form a sulfone that may more rapidly be metabolically degraded into an inactive metabolite thereby reducing the active compositions therapeutic duration of action.

In one preferred embodiment, the invention may include compound according to Formula

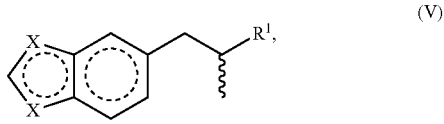

(V)

wherein:
X is S, O, or CH; and
$R^1$ is $NR^2R^3$;
$R^2$ is H or $CH_3$;
$R^3$ is $CH_3$; and
wherein said dashed lines represents possible double bond positions according to the configuration of X being S, O, or CH;
or a pharmaceutically acceptable salt thereof.

In additional embodiments, the invention may include pharmaceutical composition comprising the compound according to Formula (V), and at least one pharmaceutically acceptable carrier. The invention can further include a pharmaceutical kit containing a pharmaceutical composition including the compound of according to Formula (V), prescribing information for the composition, and a container.

As detailed below, the invention further includes methods of treating a disease or condition, and preferably a disease or condition in which modulation of serotonin receptor activity is beneficial or a shorter acting MDMA compound would be therapeutically beneficial. The method of treating a disease or condition may include administering a therapeutically-effective amount of the pharmaceutical composition according to Formula (V), to a subject in need thereof, and preferably a human subject.

The methods of treating a disease or condition if the invention may include one or more of the following therapeutic effects in a subject, namely: 1) modulating the activity of a serotonin receptor in the subject; 2) increasing serotonin levels in the subject; 2) increasing the release of dopamine and/or noradrenaline in the subject; 3) inhibiting monoamine re-uptake in the subject; and/or 3) inhibiting monoamine oxidase in a subject. Exemplary diseases or conditions that can be treated by one or more compounds of the invention may be selected from the group consisting of: schizophrenia, addiction, depression, obsessive compulsive disorder (OCD), cluster headaches, dementia, Alzheimer's disease, paralysis, attention deficit-hyperactivity disorder (ADHD), eating disorders, post-traumatic stress disorder (PTSD), anxiety, and autism.

Additional embodiments of the invention may include combination therapies comprising a compound of the invention and one or more additional active therapeutic compounds. In one preferred embodiment, this may include administering to a subject in need thereof, a therapeutically effective amount of a compositions, and preferably a pharmaceutical composition comprising the compound according to Formula (V), and at least one further therapeutic agent. Exemplary therapeutic agents can include a tryptamine compound, and an entactogen compound, or a combination of the same.

In one preferred embodiment, the invention may include a compound according to

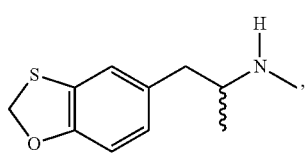
(I)

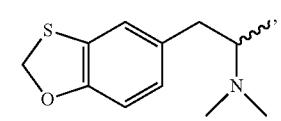
(IA)

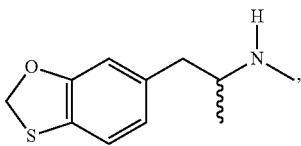
(II)

-continued

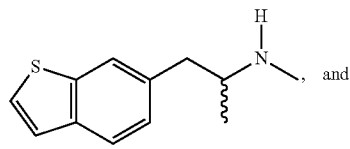
(III)
, and

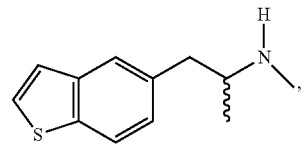
(IV)

or a pharmaceutically acceptable salt thereof.

In additional embodiment, the invention may include pharmaceutical composition comprising the compound according to Formula (V), and at least one pharmaceutically acceptable carrier. The invention can further include a pharmaceutical kit containing a pharmaceutical composition including the compound of according to Formula (I-IV), prescribing information for the composition, and a container.

As detailed below, the invention further includes methods of treating a disease or condition, and preferably a disease or condition in which modulation of serotonin receptor activity is beneficial or a shorter acting MDMA compound would be therapeutically beneficial. The method of treating a disease or condition may include administering a therapeutically-effective amount of the pharmaceutical composition according to Formula (I-IV), to a subject in need thereof, and preferably a human subject.

The methods of treating a disease or condition if the invention may include one or more of the following therapeutic effects in a subject, namely: 1) modulating the activity of a serotonin receptor in the subject; 2) increasing serotonin levels in the subject; 2) increasing the release of dopamine and/or noradrenaline in the subject; 3) inhibiting monoamine re-uptake in the subject; and/or 3) inhibiting monoamine oxidase in a subject. Exemplary diseases or conditions that can be treated by one or more compounds of the invention may be selected from the group consisting of: schizophrenia, addiction, depression, obsessive compulsive disorder (OCD), cluster headaches, dementia, Alzheimer's disease, paralysis, attention deficit-hyperactivity disorder (ADHD), eating disorders, post-traumatic stress disorder (PTSD), anxiety, and autism.

Additional embodiments of the invention may include combination therapies comprising a compound of the invention and one or more additional active therapeutic compounds. In one preferred embodiment, this may include administering to a subject in need thereof, a therapeutically effective amount of a compositions, and preferably a pharmaceutical composition comprising the compound according to Formula (I-IV), and at least one further therapeutic agent. Exemplary therapeutic agents can include a tryptamine compound, and an entactogen compound, or a combination of the same.

Additional embodiments of the invention include an enantiomeric compound or a prodrug, therapeutically active metabolite, hydrate, solvate, or pharmaceutically acceptable salt thereof having a formula according to:

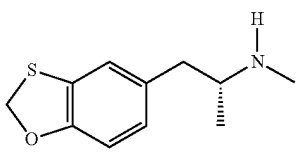

Additional embodiments of the invention include an enantiomeric compound or a prodrug, therapeutically active metabolite, hydrate, solvate, or pharmaceutically acceptable salt thereof having a formula according to:

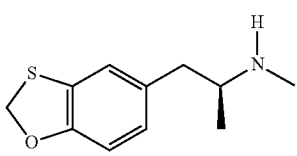

Additional embodiments of the invention include an enantiomeric compound or a prodrug, therapeutically active metabolite, hydrate, solvate, or pharmaceutically acceptable salt thereof having a formula according to:

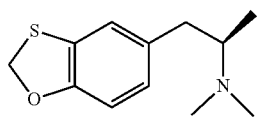

Additional embodiments of the invention include an enantiomeric compound or a prodrug, therapeutically active metabolite, hydrate, solvate, or pharmaceutically acceptable salt thereof having a formula according to:

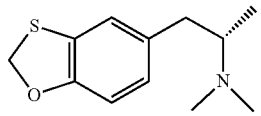

Additional embodiments of the invention include an enantiomeric compound or a prodrug, therapeutically active metabolite, hydrate, solvate, or pharmaceutically acceptable salt thereof having a formula according to:

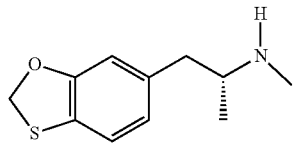

Additional embodiments of the invention include an enantiomeric compound or a prodrug, therapeutically active metabolite, hydrate, solvate, or pharmaceutically acceptable salt thereof having a formula according to:

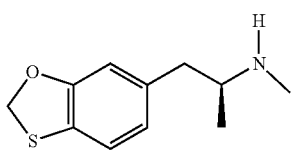

Additional embodiments of the invention include an enantiomeric compound or a prodrug, therapeutically active metabolite, hydrate, solvate, or pharmaceutically acceptable salt thereof having a formula according to:

Additional embodiments of the invention include an enantiomeric compound or a prodrug, therapeutically active metabolite, hydrate, solvate, or pharmaceutically acceptable salt thereof having a formula according to:

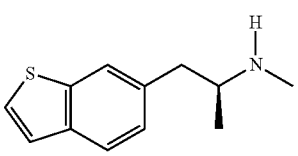

Additional embodiments of the invention include an enantiomeric compound or a prodrug, therapeutically active metabolite, hydrate, solvate, or pharmaceutically acceptable salt thereof having a formula according to:

Additional embodiments of the invention include an enantiomeric compound or a prodrug, therapeutically active metabolite, hydrate, solvate, or pharmaceutically acceptable salt thereof having a formula according to:

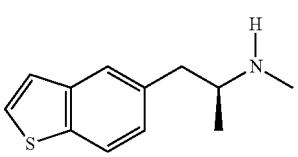

Additional embodiments of the current invention include a compound of Formula I-V, or a pharmaceutically acceptable salt, solvate, stereoisomer, tautomer, or prodrug thereof, for use in recreational, psychological, or medical therapies. One embodiment of the present invention provides a systems, methods, and compositions for novel MDMA analogs according to the compounds of Formula I-V and a pharmaceutically acceptable carrier or diluent, which may preferably further include a method of treatment of the human or animal body using one or more of the novel compounds, or pharmaceutical compositions described herein.

In another embodiment, the present invention provides the use of one or more of the novel MDMA analogs according to the compounds of Formula I-V to modulate a serotonin receptors in a subject, and preferably a human subject. In this embodiment, the compounds of Formula I-V are indirect serotonin receptor agonists. As used herein, a "serotonin receptor agonists" means a substance, and preferably a compound of the invention, having the function of acting directly or directly on a serotonin receptor causing an increase in amount of serotonin released into the synapses of a subject. As used herein, an "agonist" means a substance, and preferably a compound of the invention, having the function of binding/activating to a receptor or to produce a biological response.

In another embodiment, the present invention provides the use of one or more of the novel MDMA analogs according to the compounds of Formula I-V to increase release of dopamine and noradrenaline or inhibit monoamine re-uptake and delay metabolism by inhibition of monoamine oxidase in a subject.

In another embodiment, the present invention provides the use of one or more of the novel MDMA analogs according to the compounds of Formula I-V for the treatment of a disease or condition, and preferably a disease or condition in a subject that is may be treated by activating of one or more serotonin receptors by the agonist action of one or more compounds of the invention in a subject in need thereof.

In another embodiment, the present invention provides the use of one or more of the novel MDMA analogs according to the compounds of Formula I-V for the treatment of a disease or condition, and preferably a disease or condition in a subject that is may be treated by increasing levels of dopamine or monoamine through the action of one or more compounds of the invention in a subject in need thereof.

A compound of Formula I-V, or a pharmaceutically acceptable salt thereof, for use in the modulation of serotonin receptor activity in research, pharmaceutical, and biotechnology development. A compound of Formula I-V, or a pharmaceutically acceptable salt thereof, for use in the treatment of a disease or condition in which modulation of serotonin receptor activity is beneficial.

Additional embodiments of the invention include methods for treating a disease or condition for which comprising: administering to a subject in need thereof, a therapeutically effective amount of a combination comprising a compound of Formula I-V, or a pharmaceutically acceptable salt thereof, and at least one further therapeutic agent, wherein said further therapeutic agent is selected from the group consisting of: 1) a tryptamine compound, or a tryptamine compound and an entactogen. As used herein, "tryptamine" means compounds having affinity for a serotonin receptor and may include, but not be limited to: substituted tryptamines, psilocybin, psilocin, N,N-dimethyltryptamine, 5-methoxy-N,N-dimethyltryptamine, N,N-Dipropyltryptamine, 5-methoxy-N,N-Dipropyltryptamine, baeocystin ([3-[2-(methylamino)ethy 1]-1 H-indol-4-yl]di hydrogen phosphate), norbaeocystin ([3-(2-aminoethyl)-1H-indol-4-yl] dihydrogen phosphate), aeruguinascin (N,N,N-trimethyl-4-phosphorl-oxytryptamine), 4-acetoxy-N,N-dimethyltryptamine, 3-(2'-dimethylaminoethy 1)-4-acetoxy-indole. As used herein, "entactogens" means a compounds having the effect of releasing serotonin, norepinephrine and dopamine such as 3,4-methylenedioxyamphetamine (MDMA), 2,5-dimethoxy-4-bromophenethylamine, 3,4-methylenedioxyN-ethylamphetamine, a-lfamethyltryptamine and alpha-ethyltryptamine.

Additional embodiments of the invention include a pharmaceutical composition comprising a compound of Formula I-V, or a pharmaceutically acceptable salt thereof, for use in the treatment of a disease or condition in a subject in need thereof. A compound of the invention or pharmaceutical composition comprising the compound may be administered to a "subject," and preferably a human subject, by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. The subject may be a eukaryote, an animal, a vertebrate animal, a mammal, a rodent (e.g., a guinea pig, a hamster, a rat, a mouse), murine (e.g., a mouse), canine (e.g., a dog), feline (e.g., a cat), equine (e.g., a horse), a primate, simian (e.g., a monkey or ape), a monkey (e.g., marmoset, baboon), an ape (e.g., gorilla, chimpanzee, orangutang, gibbon), or a human.

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilizers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, diluents, excipients, etc. can be found in standard pharmaceutical texts. See, for example, "Handbook of Pharmaceutical Additives", 2nd Edition (eds. M. Ash and I. Ash), 2001 (Synapse Information Resources, Inc., Endicott, N.Y., USA), "Remington's Pharmaceutical Sciences", 20th edition, pub. Lippincott, Williams & Wilkins, 2000; and "Handbook of Pharmaceutical Excipients", 2nd edition, 1994.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary, shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrants will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet. Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet. Other conventional ingredients include anti-oxidants, colorants, flavoring agents, preservatives and taste-masking agents. Exemplary tablets contain up to about 80 wt % drug, from about 10 wt % to about 90 wt % binder, from about O wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated. The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety. Solid formulations for oral administration may be formulated to be immediate and/or modified release. Modified release formulations include delayed-, sustained-, pulsed-, controlled-, targeted and programmed release. Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include lozenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active compound.

Formulations suitable for administration by inhalation include those presented as an aerosol spray from a pressurized pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams, or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

The invention now being generally described will be more readily understood by reference to the following examples, which are included merely for the purposes of illustration of certain embodiments of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

EXAMPLES

Example 1: Compounds Synthesis Methodology

In one embodiment, the invention include methods of synthesizing the compounds according to Formulas I-V. As shown below, three of the four starting benzothiazoles and benzoxathioles are commercially available or well-precedented in the literature, which the fourth may be synthesized.

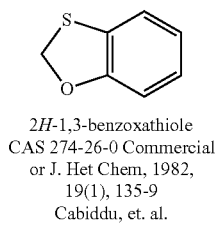

2H-1,3-benzoxathiole
CAS 274-26-0 Commercial
or J. Het Chem, 1982,
19(1), 135-9
Cabiddu, et. al.

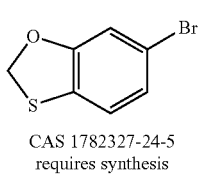

CAS 1782327-24-5
requires synthesis

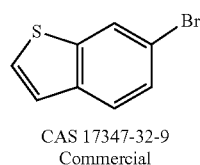

CAS 17347-32-9
Commercial

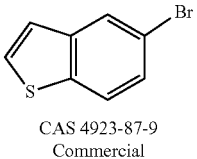

CAS 4923-87-9
Commercial

As shown below, in one embodiment, a starting ring structure compounds, in this case a benzothiazole compound can be brominated without oxidation of the sulfur. Mg or Li may react with the Br allowing the subsequent addition of a chiral aziridine which may be separately derived from an alanine compound. Titration with MeI would be used to avoid methylation of sulfur, followed by a deprotection step.

Exemplary generation of MDMA analogs

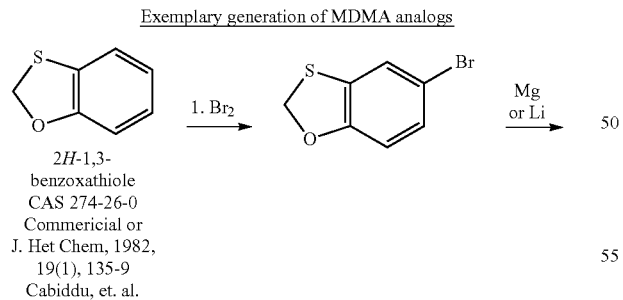

2H-1,3-
benzoxathiole
CAS 274-26-0
Commericial or
J. Het Chem, 1982,
19(1), 135-9
Cabiddu, et. al.

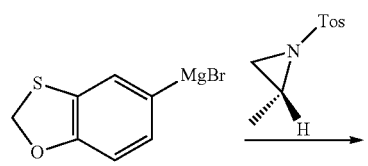

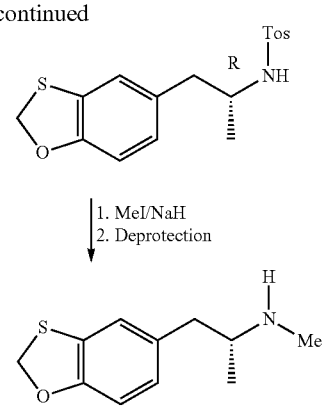

1. MeI/NaH
2. Deprotection

Example 2: Metabolic Activation of Novel Compounds

Notably, reduced sulfur compounds are prone to rapid metabolic activation. In the short-acting MDMA analog compounds of Formula(s) I-V, the sulfur is initially oxidized to a sulfone resulting in their initial inactivation. This oxidation may be accomplished by a peroxidase enzyme or an oxygenase enzyme, such as cytochrome P450 (CYP450). As shown below, in one exemplary embodiment the sulfur present in the ring of an exemplary compound according to Formula II is oxidized by CYP450 to a sulfone which is further subject to rapid downstream inactivation resulting in an inactive metabolite form.

Example step-wise metabolic activation of novel MDMA analog.

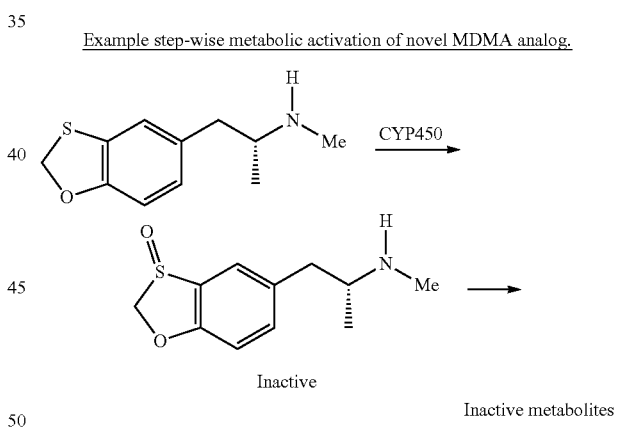

Inactive

Inactive metabolites

Notably, SAR relationships suggest the introduction of oxygen atom at the sulfur should radically alter the structure and affect binding to target receptors and transporters. In the case of the compounds according to Formulas I, and II, electrostatic and geometric computational modeling suggest sulfur substitutes for either an oxygen or mimics a methylene group, both of which are possible. In the case of the benzthiophenes, sulfur may mimic oxygen or a methylene with the Pi-system of the benzofuran ring providing a mimic of the oxygen lone pairs based on lone pair geometries.

Regardless, as noted above in either cases, the sulfone is formed and is an initial basis for inactivation. In this manner, the novel MDMA analogs of the invention exhibit a decreased half-life due to rapid metabolic inactivation. This reduction in half-life results in a shortened duration of action after administration of a therapeutically effective amount of one or more compounds of the invention to a subject in need thereof.

Example 2: Step-wise Synthesis of-1-(benzo[d][1,3]oxathiol-5-yl)-N-methylpropan-2-amine, and 1-(benzo[d][1,3]oxathiol-5-yl)-N,N-dimethylpropan-2-amine As shown in Scheme 1 below, the present invention provides for the step-wise synthesis of the compound according to MY100 (Formula I) and MY101 (Formula IA):

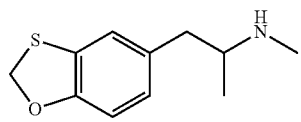
MY100

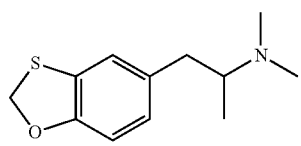
MY101 according to the following scheme:

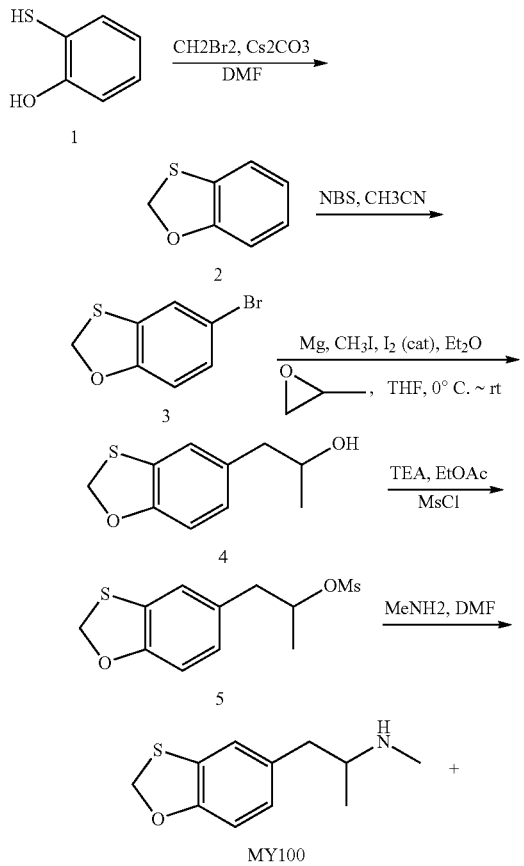

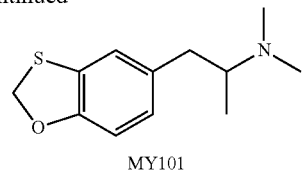
MY101

As described in Scheme 1, the present inventors demonstrated the synthesis of precursor compound benzo[d][1,3]oxathiole (2).

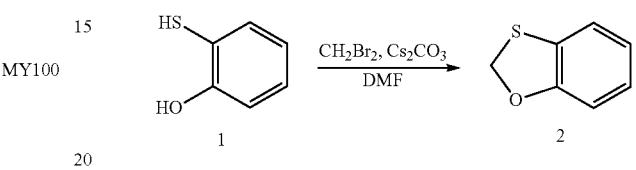

In this embodiment, to a solution of dibromomethane (9.7 g, 75 mmol) in dry DMF (120 mL), solid Cs$_2$CO$_3$ (24.4 g, 75 mmol) was added, and the resulted suspension was placed in an oil bath preheated to 100° C. The reaction mixture was vigorously stirred, and when the temperature inside the flask reached 60° C., a solution of 2-hydroxythiophenol 1 (6.3 g, 50 mmol) in DMF (30 mL) was added dropwise within 1 h. Temperature inside the flask quickly reached 95-98° C. and it was maintained at this level during addition. After the addition was complete, stirring at 95-98° C. was continued for 4 h. The reaction mixture was cooled to the room temperature, poured into water (450 mL), and the aqueous phase (pH=9) was extracted with diethyl ether. The combined organic extracts were washed with water (50 mL), dried over Na$_2$SO$_4$, and concentrated under reduced pressure to give pale yellow oil (8.59 g). The crude mixture was purified by flash column chromatography (silica gel, Hexans: Et2O=50:1) to provide compound 2 (5.01 g, 72% yield) as a colorless oil. $^1$H NMR (400 MHz, CDCl$_3$): δ 7.20 (dd, J=7.6 Hz and 1.2 Hz, 1H), 7.03 (m, 1H), 6.91 (m, 1H), 6.85 (dd, J=7.9 Hz and 0.9 Hz, 1H), 5.71 (s, 2H).

As described in Scheme 1, the present inventors demonstrated the synthesis of precursor compound 5-bromobenzo[d][1,3]oxathiole (3).

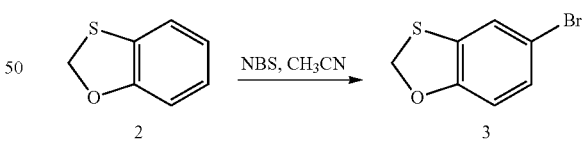

In this embodiment, to a stirred solution of benzo[d][1,3]oxathiole 2 (3.0 g, 21.7 mmol) in anhydrous acetonitrile (50 mL), solid N-bromosuccinimide (4.2 g, 23.6 mmol) was added portionwise at room temperature during ~5 min (minor heat evolution, the solution become orange). Stirring at room temperature was continued for 30 min, then the reaction mixture was diluted with diethyl ether (100 mL) and stirred with 10% aqueous sodium thiosulfate solution (20 mL) for few minutes. After this the organic layer become almost colorless, the organic layer was separated, washed with water (10 mL), brine (10 mL), dried over Na$_2$SO$_4$ and concentrated under reduced pressure to give yellow oil (5.64 g). The crude mixture was purified by flash column chromatography (silica gel, Hexans: Et$_2$O=50:1) to provide compound 3 (3.45 g 73% yield) as a colorless oil. $^1$H NMR (400 MHz, CDCl$_3$): δ 7.28 (d, J=2.1 Hz, 1H), 7.11 (dd, J=8.5 Hz and 2.1 Hz, 1H), 6.70 (d, J=8.5 Hz, 1H), 5.72 (s, 2H).

As described in Scheme 1, the present inventors demonstrated the synthesis of precursor compound 1-(benzo[d][1,3]oxathiol-5-yl)propan-2-ol (4).

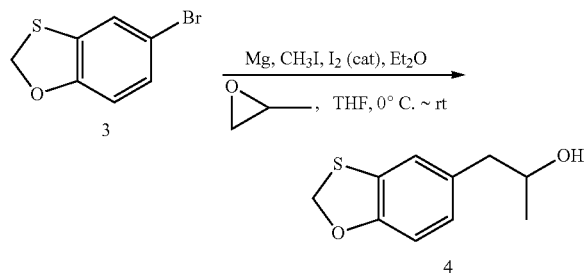

In this embodiment, to a pre-dried 3-neck flask, containing magnesium turnings (1.36 g, 56 mmol), suspended in anhydrous diethyl ether (15 mL), iodine (39 mg, 0.14 mmol) was added at room temperature under nitrogen. To this mixture, a solution of 5-bromobenzo[d][1,3]oxathiole 3 (1.2 g, 5.6 mmol) and methyl iodide (4.0 g, 1.8 mL, 28 mmol) in anhydrous diethyl ether (15 mL) was added gradually at room temperature. After the addition was complete, boiling of the reaction mixture was maintained for 1 h, and then the formed Grignard reagent solution was allowed to cool to the room temperature.

To this Grignard reagent was added propylene oxide (3.9 g, 4.7 mL, 67.2 mmol), copper(I) iodide (110 mg, 0.58 mmol). The reaction mixture was allowed to warm gradually to the room temperature and left stirring overnight. The reaction mixture was diluted with diethyl ether (20 mL) and quenched with saturated aqueous solution of ammonium chloride. The blue aqueous layer (pH=4) was separated and extracted with ethyl acetate (20 mL). The combined organic extracts were washed with water (20 mL), brine (20 mL), dried over Na$_2$SO$_4$ and concentrated under reduced pressure to give pale yellow oil (5.89 g). The crude mixture was purified by flash column chromatography (silica gel, Hexans: EtOAc=5:1 to 3:1) to provide compound 4 (0.70 g, 64% yield) as a colorless oil. $^1$H NMR (400 MHz, CDCl$_3$): δ 7.06 (d, J 1.8 Hz, 1H), 6.85 (dd, J=8.1 Hz and 1.8 Hz, 1H), 6.78 (d, J 8.1 Hz, 1H), 5.69 (s, 2H), 3.98 (m, 1H), 2.72 (dd, J$_{AB}$=13.6 Hz, J=4.7 Hz, 1H), 2.61 (dd, J$_{AB}$=13.6 Hz, J=7.9 Hz, 1H), 1.55 (br s, 1H), 1.25 (d, J=6.2 Hz, 3H). $^{13}$C NMR (CDCl$_3$): d 155.0, 132.9, 126.9, 126.1, 123.1, 110.1, 75.3, 68.9, 45.0, 22.8.

As described in Scheme 1, the present inventors demonstrated the synthesis of precursor compound 1-(benzo[d][1,3]oxathiol-5-yl)propan-2-yl methanesulfonate (5).

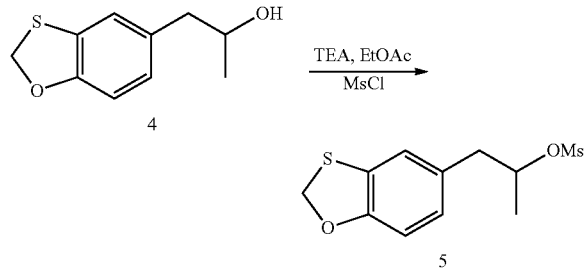

In this embodiment, to a stirred solution of 1-(benzo[d][1,3]oxathiol-5-yl)propan-2-ol 4 (0.70 g, 3.57 mmol) and triethylamine (0.6 mL, 4.46 mmol) in ethyl acetate (12 mL), cooled in an ice bath, a solution of methanesulfonyl chloride (0.45 g, 3.93 mmol) in ethyl acetate (3 mL) was added dropwise within 3 min. The white precipitate started to form when methanesulfonyl chloride addition begun. After 30 min the ice bath was removed and stirring was continued at room temperature for 1.5 h. The reaction mixture was diluted with ethyl acetate (20 mL) and quenched with addition of water (10 mL). The organic layer was separated, washed with 2N HCl (10 mL), water (10 mL), saturated aqueous NaHCO$_3$(10 mL), brine (10 mL), dried over Na$_2$SO$_4$ and concentrated under reduced pressure to give a title compound 5 (0.96 g, 98% yield) as a thick pale-yellow oil. $^1$H NMR (400 MHz, CDCl$_3$): δ 7.06 (d, J=1.8 Hz, 1H), 6.87 (dd, J=8.1 Hz and 1.8 Hz, 1H), 6.78 (d, J=8.1 Hz, 1H), 5.70 (s, 2H), 4.86 (m, 1H), 2.93 (dd, J$_{AB}$=14.1 Hz, J=7.8 Hz, 1H), 2.83 (dd, J$_{AB}$=14.1 Hz, J=5.5 Hz, 1H), 2.69 (s, 3H), 1.46 (d, J=6.2 Hz, 3H).

As described in Scheme 1, the present inventors demonstrated the synthesis of 1-(benzo[d][1,3]oxathiol-5-yl)-N-methylpropan-2-amine (MY100 or Formula I), and 1-(benzo[d][1,3]oxathiol-5-yl)-N,N-dimethylpropan-2-amine (MY101 or Formula IA).

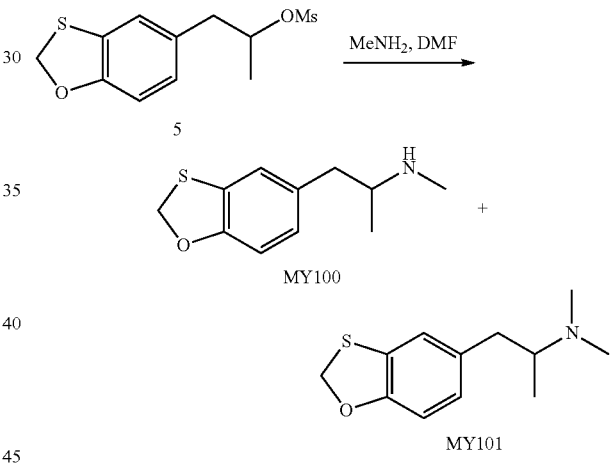

In this embodiment, to a stirred solution of 1-(benzo[d][1,3]oxathiol-5-yl)propan-2-yl methanesulfonate 5 (0.23 g, 0.83 mmol) in N,N-dimethylformamide (2.5 mL), a solution of methylamine (2.5 mL of 40% aqueous solution, 29 mmol) was added, the reaction flask was sealed and stirred at 50° C. for 20 h. The reaction mixture was partitioned between ethyl acetate (30 mL) and water (20 mL). The aqueous layer (pH=11) was separated and extracted with ethyl acetate (15 mL). The combined organic extracts were washed with water (10 mL), brine (10 mL), dried over Na$_2$SO$_4$ and concentrated under reduced pressure to give pale yellow oil (0.33 g). The crude mixture was purified by flash column chromatography on silica gel using chloroform—7N ammonia solution in methanol in 30:1 ratio.

The title MY100 (75 mg, 43% yield) was obtained as a colorless oil. $^1$H NMR (400 MHz, CDCl$_3$): δ 7.02 (d, J=1.7 Hz, 1H), 6.82 (dd, J=8.1 Hz and 1.7 Hz, 1H), 6.76 (d, J=8.1 Hz, 1H), 5.68 (s, 2H), 2.75 (m, 1H), 2.65 (dd, J$_{AB}$=13.4 Hz, J=7.0 Hz, 1H), 2.54 (dd, J$_{AB}$=13.4 Hz, J=6.3 Hz, 1H), 2.42

(s, 3H), 1.87 (br s, 1H), 1.06 (d, J=6.2 Hz, 3H). $^{13}$C NMR (100 MHz, CDCl$_3$): δ 154.4, 133.8, 126.8, 125.9, 122.9, 110.0, 75.2, 56.4, 42.7, 33.9, 19.6.

The title MY101 (14 mg, 8% yield) was isolated from the preceding fractions as a colorless oil. $^1$H NMR (400 MHz, CDCl$_3$): δ 7.05 (d, J=1.6 Hz, 1H), 6.83 (dd, J=8.1 Hz and 1.6 Hz, 1H), 6.75 (d, J=8.1 Hz, 1H), 5.68 (2H, s), 3.27 (dd, J$_{AB}$=12.8 Hz, J=3.1 Hz, 1H), 3.18 (m, 1H), 2.61 (s, 3H), 2.43 (dd, J$_{AB}$=12.8 Hz, J=10.5 Hz, 1H), 1.13 (d, J=6.5 Hz, 3H). $^{13}$C NMR (100 MHz, CDCl$_3$): δ 155.2, 131.7, 126.8, 126.4, 122.9, 110.2, 75.4, 62.5, 39.6, 37.6, 12.7.

Example 3: Step-wise synthesis of 1-(benzo[d][1,3]oxathiol-6-yl)-N-methylpropan-2-amine As shown in Scheme 2 below, the present invention provides for the step-wise synthesis of the compound according to MY200 (Formula II):

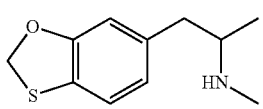

MY200 according to the following scheme:

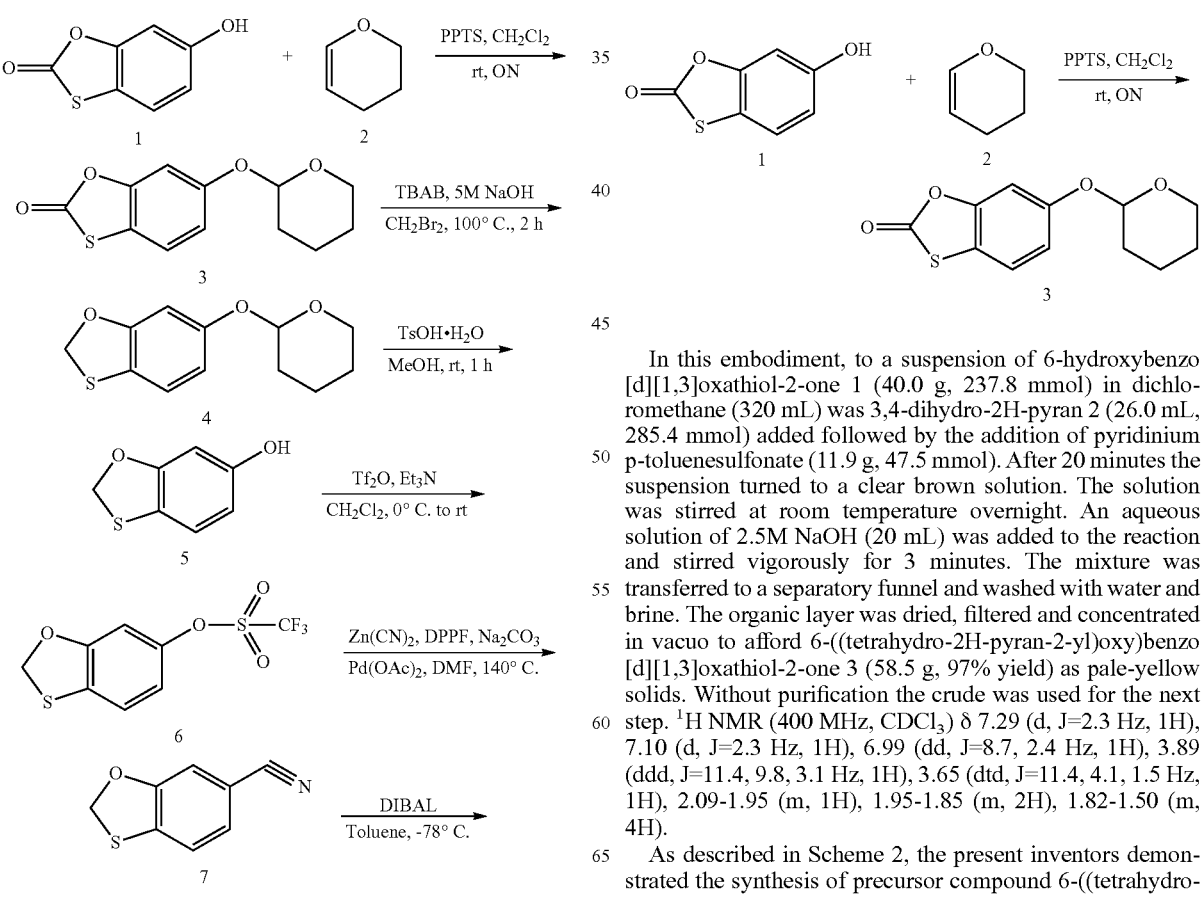

As described in Scheme 2, the present inventors demonstrated the synthesis of precursor compound 6-((tetrahydro-2H-pyran-2-yl)oxy)benzo[d][1,3]oxathiol-2-one (3).

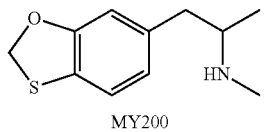

In this embodiment, to a suspension of 6-hydroxybenzo[d][1,3]oxathiol-2-one 1 (40.0 g, 237.8 mmol) in dichloromethane (320 mL) was 3,4-dihydro-2H-pyran 2 (26.0 mL, 285.4 mmol) added followed by the addition of pyridinium p-toluenesulfonate (11.9 g, 47.5 mmol). After 20 minutes the suspension turned to a clear brown solution. The solution was stirred at room temperature overnight. An aqueous solution of 2.5M NaOH (20 mL) was added to the reaction and stirred vigorously for 3 minutes. The mixture was transferred to a separatory funnel and washed with water and brine. The organic layer was dried, filtered and concentrated in vacuo to afford 6-((tetrahydro-2H-pyran-2-yl)oxy)benzo[d][1,3]oxathiol-2-one 3 (58.5 g, 97% yield) as pale-yellow solids. Without purification the crude was used for the next step. $^1$H NMR (400 MHz, CDCl$_3$) δ 7.29 (d, J=2.3 Hz, 1H), 7.10 (d, J=2.3 Hz, 1H), 6.99 (dd, J=8.7, 2.4 Hz, 1H), 3.89 (ddd, J=11.4, 9.8, 3.1 Hz, 1H), 3.65 (dtd, J=11.4, 4.1, 1.5 Hz, 1H), 2.09-1.95 (m, 1H), 1.95-1.85 (m, 2H), 1.82-1.50 (m, 4H).

As described in Scheme 2, the present inventors demonstrated the synthesis of precursor compound 6-((tetrahydro-2H-pyran-2-yl)oxy)benzo[d][1,3]oxathiole (4).

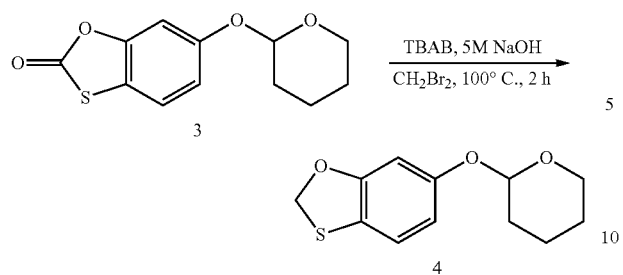

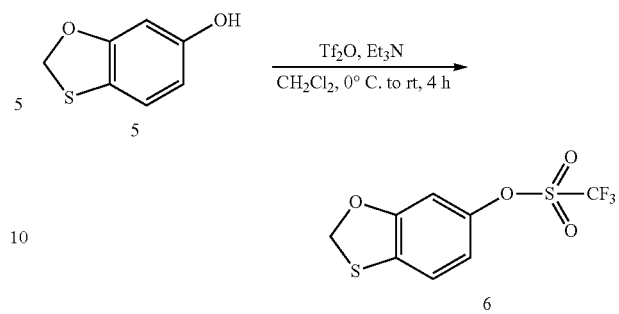

In this embodiment, to a solution of 6-((tetrahydro-2H-pyran-2-yl) oxy)benzo[d][1,3]oxathiol-2-one 3 (58.5 g, 231.8 mmol) in dibromoethane (163 mL) was 5M NaOH (231 mL, 1159 mmol) added followed by the addition of tetrabutylammonium bromide (7.5 g, 23.2 mmol). The mixture was stirred vigorously at 100° C. for 2 hours. The reaction was cooled to room temperature and transferred to a separatory funnel. The separated organic layer was filtered through celite. The filtrate was washed with water and brine and the organic layer was dried, filtered and concentrated in vacuo to afford 6-((tetrahydro-2H-pyran-2-yl)oxy)benzo[d][1,3]oxathiole 4 (54.3 g, 98% yield) as a thick dark yellow oil. $^1$H NMR (400 MHz, CDCl$_3$) δ 7.04 (dd, J=8.1, 0.6 Hz, 1H), 6.67-6.59 (m, 2H), 5.69 (s, 2H), 3.91 (ddd, J=11.4, 9.4, 3.1 Hz, 1H), 3.61 (dtd, J=11.4, 4.2, 1.6 Hz, 1H), 2.07-1.92 (m, 1H), 1.91-1.78 (m, 2H), 1.75-1.54 (m, 4H).

As described in Scheme 2, the present inventors demonstrated the synthesis of precursor compound benzo[d][1,3]oxathiol-6-ol (5).

In this embodiment, to a solution of benzo[d][1,3]oxathiol-6-ol 5 (1.75 g, 11.40 mmol) in dichloromethane (15 mL) at 0° C. was triethylamine (2.4 mL, 17.09 mmol) added followed by a dropwise addition of trifluoromethanesulfonic anhydride (2.1 mL, 12.53 mmol). The temperature was raised to room temperature and stirred for 4 hours. The reaction mixture was transferred to a separatory funnel and washed with NaHCO$_3$(10 mL×3). The organic layer was dried, filtered and concentrated in vacuo. The crude material was purified by plug column chromatography (100% DCM) to afford benzo[d][1,3]oxathiol-6-yl trifluoromethanesulfonate 6 (2.93 g, 89% yield) as dark red solids. $^1$H NMR (400 MHz, CDCl$_3$) δ 7.19 (d, J=8.4 Hz, 1H), 6.83 (dd, J=8.4, 2.4 Hz, 1H), 6.77 (d, J=2.3 Hz, 1H), 5.82 (s, 2H).

As described in Scheme 2, the present inventors demonstrated the synthesis of precursor compound benzo[d][1,3]oxathiole-6-carbonitrile (7).

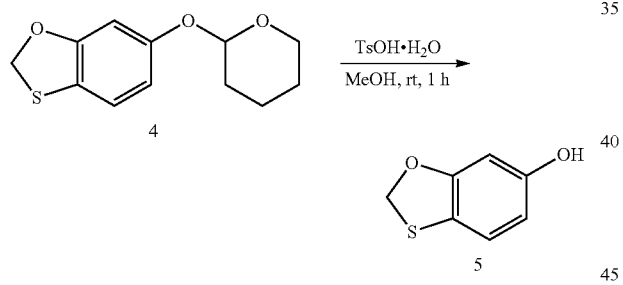

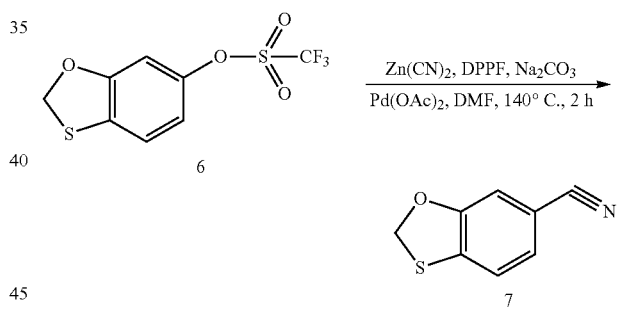

In this embodiment, to a solution of 6-((tetrahydro-2H-pyran-2-yl)oxy)benzo[d][1,3]oxathiole 4 (54.3 g, 227.8 mmol) in methanol (455 mL) at room temperature was added p-toluenesulfonic acid monohydrate (4.3 g, 22.8 mmol). The reaction was stirred for 1 hour and monitored by TLC. The solution was passed through celite and filtrate was concentrated in vacuo to afford a thick black oil. The oil was washed with ethyl acetate (200 mL) by vigorous stirring to extract the crude product. Process was repeated until TLC showed all crude material was extracted from the thick black oil. The decanted organic solutions were passed through celite and the filtrate was concentrated in vacuo to afford a dark oil. The oil was purified by column chromatography (5-20% ethyl acetate/hexane) to yield benzo[d][1,3]oxathiol-6-ol 5 (8.0 g, 23% yield) as a yellow oil. $^1$H NMR (400 MHz, CDCl$_3$) δ 7.00 (d, J=8.1 Hz, 1H), 6.47-6.36 (m, 2H), 5.70 (s, 2H).

As described in Scheme 2, the present inventors demonstrated the synthesis of precursor compound benzo[d][1,3]oxathiol-6-yl trifluoromethanesulfonate (6).

In this embodiment, to a solution of benzo[d][1,3]oxathiol-6-yl trifluoromethanesulfonate 6 (2.90 g, 10.19 mmol) in DMF (72 mL) was degassed with N$_2$ for 15 minutes. Under N$_2$ atmosphere was zinc chloride (1.19 g, 10.13 mmol), 1,1'-Ferrocenediyl-bis(diphenylphosphine) (2.81 g, 5.06 mmol), sodium carbonate (1.07 g, 10.13 mmol), and palladium (II) acetate (0.45 g, 2.02 mmol) added respectively. The flask was capped then refluxed at 140° C. for 2 hours. The mixture was diluted with ethyl acetate (50 mL) and filtered through celite. The filtrate was washed with water (50 mL×3) and the organic layer was dried, filtered and concentrated in vacuo. The crude was purified by column chromatography (0-5% ethyl acetate/hexane) to yield benzo[d][1,3]oxathiole-6-carbonitrile 7 (1.2 g, 72% yield) as pale-yellow solids. $^1$H NMR (400 MHz, CDCl$_3$) δ 7.25 (d, J=7.9 Hz, 1H), 7.20 (dd, J=7.9, 1.5 Hz, 1H), 7.03 (d, J=1.5 Hz, 1H), 5.81 (s, 2H).

As described in Scheme 2, the present inventors demonstrated the synthesis of precursor compound benzo[d][1,3]oxathiole-6-carbaldehyde (8).

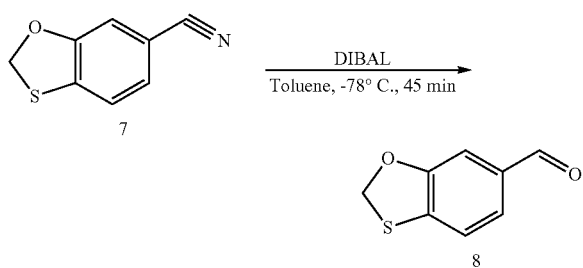

In this embodiment, to a solution of benzo[d][1,3]oxathiole-6-carbonitrile 7 (1.0 g, 6.12 mmol) in toluene (35 mL) at −78° C. was diisobutylaluminium hydride (9.2 mL, 9.19 mmol) added dropwise. The reaction was kept at −78° C. for 45 minutes. Water (0.36 mL) was added to the reaction followed by the addition of 4M NaOH (0.36 mL), and water (0.9 mL) in the respective order at −78° C. The mixture was stirred at the same temperature for 30 minutes then raised to room temperature and stirred for another 30 minutes. Then sodium sulphate was added and left to stir for 15 minutes. The mixture was then filtered through celite, and the solids washed with ethyl acetate. The filtrate was transferred to a separatory funnel and washed with water and brine. The organic layer was dried, filtered and concentrated in vacuo. The crude was purified by column chromatography (5-10% hexane/DCM) to afford benzo[d][1,3]oxathiole-6-carbaldehyde 8 (0.87 g, 85% yield) as pale-yellow solids. $^1$H NMR (400 MHz, CDCl$_3$) δ 9.88 (s, 1H), 7.43 (dd, J=7.8, 1.5 Hz, 1H), 7.33-7.27 (m, 2H), 5.81 (s, 2H).

As described in Scheme 2, the present inventors demonstrated the synthesis of precursor compound 2-(benzo[d][1,3]oxathiol-6-yl)acetaldehyde (9).

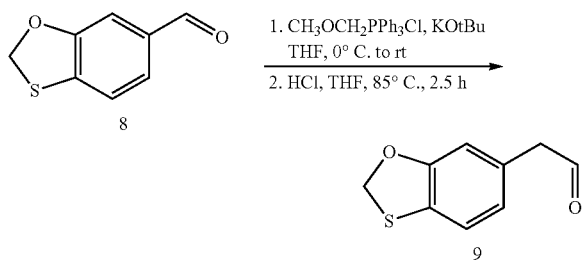

In this embodiment, to a suspension of the Wittig reagent (2.86 g, 8.34 mmol) in THF (7.0 mL) at 0° C. was added potassium tert-butoxide (0.61 g, 5.40 mmol) portion wise to form a dark red suspension. The mixture was stirred at 0° C. for 20 min then raised to room temperature for another 20 minutes. The mixture was cooled to 0° C. and a solution of benzo[d][1,3]oxathiole-6-carbaldehyde 8 (0.88 g, 4.91 mmol) in THF (7.0 mL) was added to the reaction and the yellow suspension was stirred at room temperature for 1 hour. The reaction was quenched with water and extracted with ethyl acetate. The organic layer was dried, filtered, and concentrated in vacuo. The crude intermediate was purified by column chromatography (5-10% ethyl acetate/hexane) to yield 6-(2-methoxyvinyl) benzo-[d][1,3]oxathiole vinyl ether (1.10 g) as a yellow oil. This compound was used for next step without further characterization.

In this embodiment, to a solution of 6-(2-methoxyvinyl) benzo[d][1,3]oxathiole (1.10 g, 5.94 mmol) in THF (18 mL) at 0° C. was 2M HCl (18 mL, 35.6 mmol) added and refluxed at 85° C. for 2 hours. The mixture was diluted with ethyl acetate (53 mL) and extracted. The organic layer was washed with water (32 mL×2), a diluted solution of sodium bicarbonate (pH 8) (32 mL), and then brine (32 mL). The combined organic layer was dried, filtered and concentrated in vacuo. The crude material was purified by column chromatography (5-20% ethyl acetate/hexane) to yield 2-(benzo[d][1,3]oxathiol-6-yl)acetaldehyde 9 (0.32 g, 32% yield) as a yellow oil. $^1$H NMR (400 MHz, CDCl$_3$) δ 9.73 (t, J=2.3 Hz, 1H), 7.17 (d, J=7.8 Hz, 1H), 6.79-6.73 (m, 1H), 6.71 (d, J=1.7 Hz, 1H), 5.73 (s, 2H), 3.63 (d, J=2.3 Hz, 2H).

As described in Scheme 2, the present inventors demonstrated the synthesis of precursor compound 1-(benzo[d][1,3]oxathiol-6-yl)propan-2-ol (10).

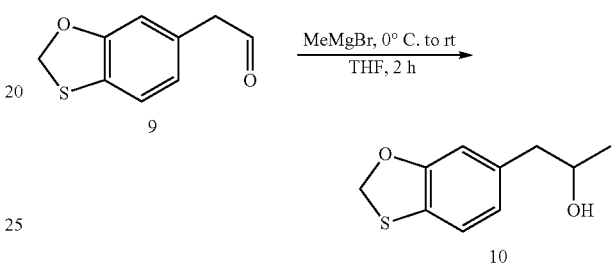

In this embodiment, to a solution a solution of 2-(benzo[d][1,3]oxathiol-6-yl)acetaldehyde 9 (0.29 g, 1.63 mmol) in THF (9.5 mL) at 0° C. was methyl magnesium bromide 3M in diethyl ether (0.65 mL, 1.964 mmol) added dropwise. The reaction was raised to room temperature and stirred for 2 hours. The mixture was then poured over crushed ice water (14 mL). To the cold mixture was 0.1M HCl (2.9 mL) added and stirred for 5 minutes. The aqueous was extracted with ethyl acetate and the organic layer was dried, filtered and concentrated in vacuo to afford 1-(benzo[d][1,3]oxathiol-6-yl)propan-2-ol 10 (0.147 g, 46% yield) as a yellow oil. $^1$H NMR (400 MHz, CDCl$_3$) δ 7.12 (d, J=7.7 Hz, 1H), 6.76 (dd, J=7.7, 1.6 Hz, 1H), 6.73 (d, J=1.7 Hz, 1H), 5.70 (s, 2H), 4.05-3.95 (m, 1H), 2.73 (dd, J=13.6, 4.8 Hz, 1H), 2.63 (dd, J=13.5, 8.0 Hz, 1H), 1.25 (d, J=6.2 Hz, 3H).

As described in Scheme 2, the present inventors demonstrated the synthesis of precursor compound 1-(benzo[d][1,3]oxathiol-6-yl)propan-2-yl methanesulfonate (11).

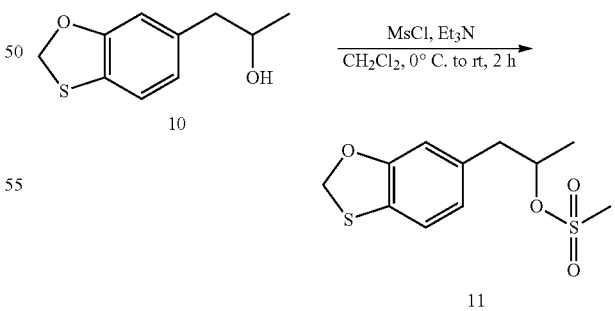

In this embodiment, to a solution of 1-(benzo[d][1,3]oxathiol-6-yl)propan-2-ol 10 (0.147 g, 0.747 mmol) in dichloromethane (3.7 mL) was triethylamine (0.13 mL, 0.934 mmol) added followed by the addition methanesulfonyl chloride (0.064 mL, 0.822 mmol) dropwise. The reaction was raised to room temperature and stirred for 2 hours. The mixture was then cooled to 0° C., quenched with ice cold water and transferred to separatory funnel. The organic layer was washed with water (10 mL×3) and brine, then dried, filtered and concentrated in vacuo to obtain 1-(benzo[d][1,3]oxathiol-6-yl)propan-2-yl methanesulfonate 11 (0.201 g, 98% yield) as a yellow oil. Without purification the crude was used for the next step. $^1$H NMR (400 MHz, CDCl$_3$) δ 7.13 (d, J=7.8 Hz, 1H), 6.78 (dd, J=7.7, 1.7 Hz, 1H), 6.73 (d, J=1.8 Hz, 1H), 5.71 (s, 2H), 4.94-4.83 (m, 1H), 2.94 (dd, J=14.0, 7.6 Hz, 1H), 2.84 (dd, J=14.0, 5.5 Hz, 1H), 2.71 (s, 3H), 1.46 (d, J=6.2 Hz, 3H).

As described in Scheme 2, the present inventors demonstrated the synthesis of 1-(benzo[d][1,3]oxathiol-6-yl)-N-methylpropan-2-amine (MY200 or Formula II).

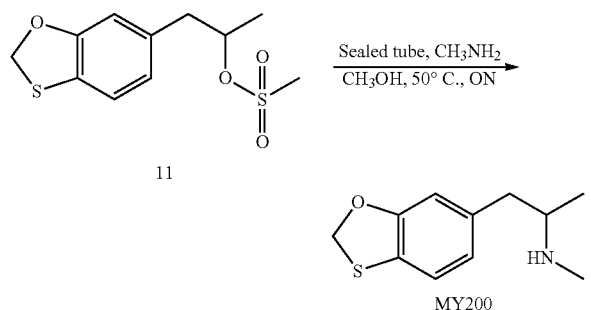

In this embodiment, to a sealed tube was a solution of 1-(benzo[d][1,3]oxathiol-6-yl)propan-2-yl methanesulfonate 11 (0.21 g, 0.75 mmol) in methanol (2.0 mL) added and cooled to 0° C. Methylamine (40% aqueous) (2.0 mL, 26.3 mmol) was added to the solution and the tube was sealed and raised to room temperature then heated at 50° C. overnight. The reaction mixture was transferred to a round bottomed flask and the solvent evaporated. The crude material was loaded on a silica gel column for purification (0-10% ammonia solution in methanol (5%)/dichloromethane) to afford 1-(benzo[d][1,3]oxathiol-6-yl)-N-methylpropan-2-amine MY200 (0.063 g, 40% yield) as a yellow oil. $^1$H NMR (400 MHz, CDCl$_3$) δ 7.10 (d, J=7.7 Hz, 1H), 6.73 (dd, J=7.7, 1.7 Hz, 1H), 6.70 (d, J=1.7 Hz, 1H), 5.69 (s, 2H), 2.83-2.71 (m, 1H), 2.65 (dd, J=13.4, 7.0 Hz, 1H), 2.56 (dd, J=13.4, 6.3 Hz, 1H), 2.41 (s, 3H), 1.07 (d, J=6.2 Hz, 3H). $^{13}$C NMR (100 MHz, CDCl$_3$) δ 156.41, 137.93, 123.47, 123.21, 121.94, 111.22, 75.29, 56.30, 43.05, 33.97, 19.66. MS (ESI) m/z: [M+H]$^+$ Calcd for C$_{11}$H$_{15}$NOS 210.09; found 210. HPLC purity 96.62%.

Example 4: Alternative Synthesis of MY 200 (Formula II)

As shown in exemplary Scheme 2 below, in one embodiment, the invention includes methods of synthesizing the compound according to MY200 (Formula II):

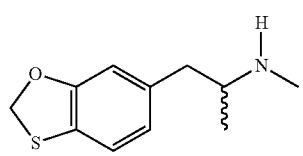
MY200 (Formula II)

In a preferred embodiment, the compound according to MY200 (Formula II) can be synthesized according to the scheme 2A and/or 2B, or 2C:

MY200 Synthesis Scheme 2A

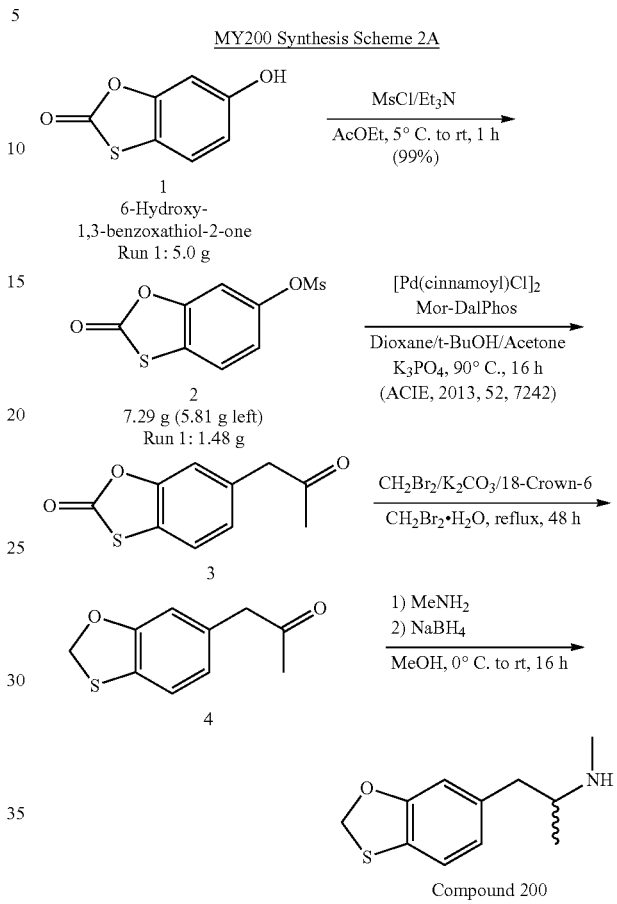

According to Step 1 of synthesis scheme 2, the present inventors demonstrated the synthesis of 2-oxo-1,3-benzoxathiol-6-yl methanesulfonate (2) (compound 2) according to the step:

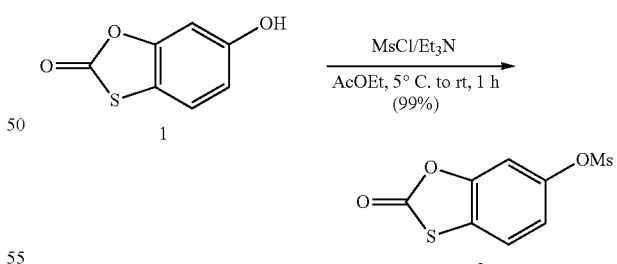

In this embodiment, to a stirred solution of 6-hydroxy1,3-benzoxathiol-2-one (1, 5.0 g, 29.7 mmol) and triethylamine (3.75 g, 5.2 mL, 37.1 mmol) in ethyl acetate (50 mL), cooled in an ice bath, a solution of methanesulfonyl chloride (3.75 g, 32.7 mmol) in ethyl acetate (10 mL) was added dropwise in 5 min. The white precipitate stared to appear quickly when addition begun. When the addition of methanesulfonyl chloride was complete, the ice bath was removed and stirring was continued at room temperature for 1 h. The reaction mixture was diluted with ethyl acetate (100 mL) and quenched with the addition of water (50 mL). The organic layer was separated, washed with 2N HCl (20 mL), water (20 mL), saturated aqueous $NaHCO_3$ (20 mL), water (20 mL), brine (20 mL), dried over $Na_2SO_4$ and concentrated under reduced pressure to give the title compound (2) as a colorless solid. Yield 7.29 g (99%). The material was used in the following step without further purification. 1H NMR ($CDCl_3$, δ, ppm): 7.48 (1H, d, J=8.6 Hz); 7.32 (1H, d, J=2.3 Hz); 7.25 (1H, dd, J=8.6 Hz and 2.3 Hz); 3.23 (3H, s).

According to alternative embodiment of synthesis scheme 2, being a the present inventors demonstrated the synthesis of 2-oxo-1,3-benzoxathiol-6-yl 1H-imidazole-1-sulfonate (2):

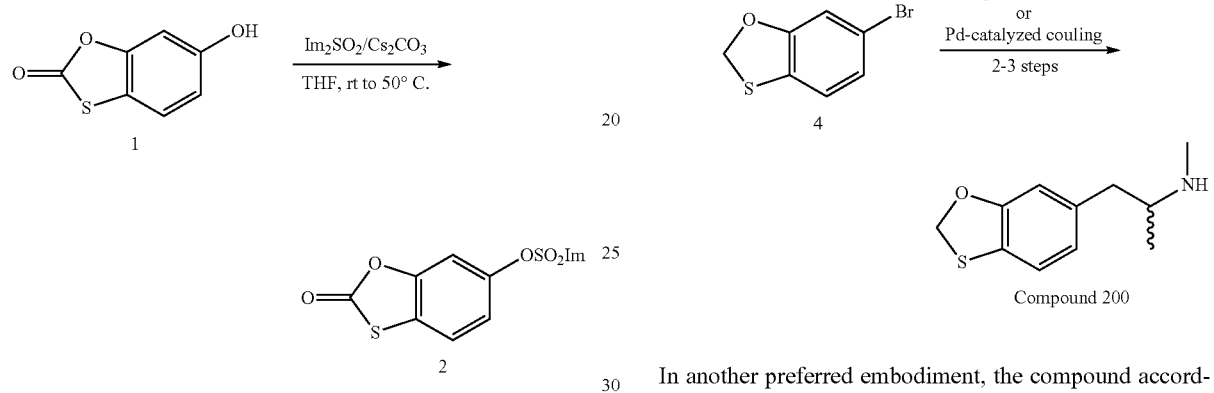

In this embodiment, to a stirred solution of 6-hydroxy1,3-benzoxathiol-2-one (1, 3.36 g, 20.0 mmol) and 1.1'-sulfonyldiimidazole (4.96 g, 25.0 mmol) in tetrahydrofuran (70 mL), solid $Cs_2CO_3$ (4.07 g, 12.5 mmol) was added at room temperature, and the resulted suspension was stirred at room temperature for 16 h and at 50° C. for 1 h. The reaction mixture was concentrated under reduced pressure and the residue was partitioned between ethyl acetate (60 mL) and water (20 mL) giving two clear layers (aqueous layer pH=9). The organic layer was separated, washed with water (20 mL), saturated aqueous $NH_4Cl$ (20 mL), brine (10 mL), dried over $Na_2SO_4$ and concentrated under reduced pressure to give a yellow oil (6.27 g). The crude mixture was purified by flash column chromatography on silica gel using chloroform—ethyl acetate mixture in 20:1 ratio as a mobile phase. The title compound 2 (Rf ~0.2) was obtained as a colorless solid. Yield 0.91 g (15%). 1H NMR($CDCl_3$, δ, ppm): 7.79 (11H, s); 7.42 (11H, d, J=8.6 Hz); 7.35 (11H, t, J=1.5 Hz); 7.23 (1H, m); 7.03 (11H, d, J=2.4 Hz); 6.84 (11H, dd, J=8.6 Hz and 2.4 Hz).

In another preferred embodiment, the compound according to MY200 (Formula II) can be synthesized according to the scheme 2B3:

In another preferred embodiment, the compound according to MY200 (Formula II) can be synthesized according to the scheme 2C:

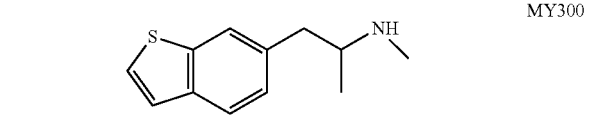

Example: Step-Wise Synthesis of 1-(benzo[b]thiophen-6-yl)-N-methylpropan-2-amine hydrochloride As shown in Scheme 3 below, the present invention provides for the step-wise synthesis of the compound according to MY300 (Formula III):

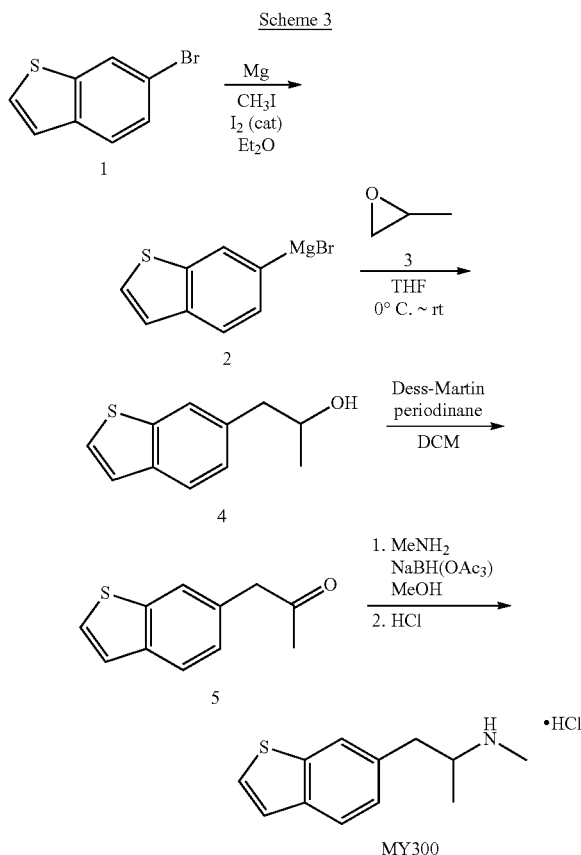

according to the following scheme:

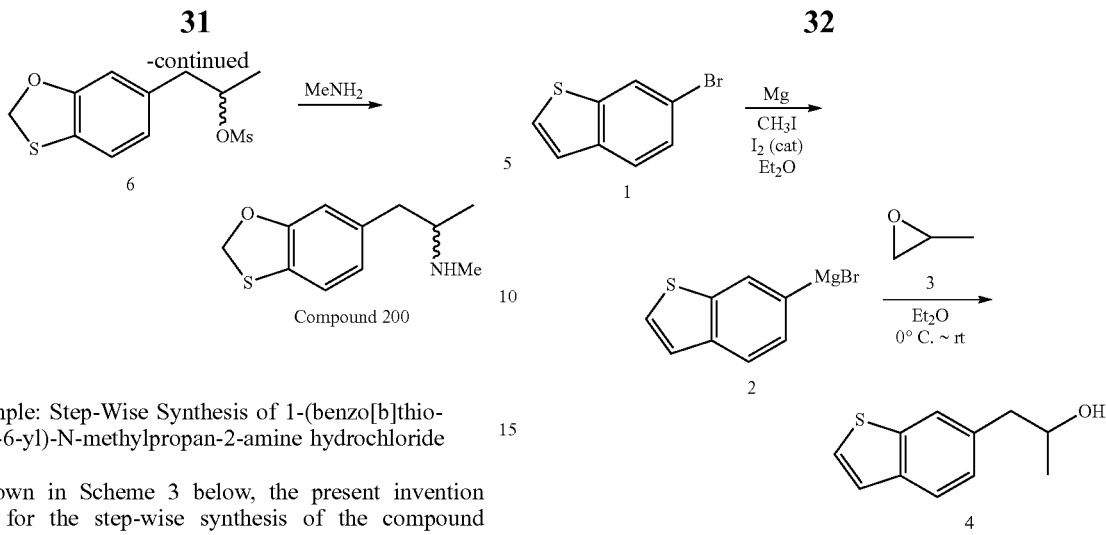

In this embodiment, to a pre-dried 3-neck flask equipped with a condenser, additional funnel and thermometer under nitrogen was charged magnesium turnings (0.5 g, 20.5 mmol), iodine (14 mg, 0.055 mmol) and diethyl ether (4 mL, anhydrous). To this stirred reaction mixture was added 0.4 mL of solution of 6-bromobenzo[b]thiophene 1 (0.42 g, 1.97 mmol), iodomethane (1.4 g, 9.86 mmol) in anhydrous $Et_2O$ (4 mL). After a few minutes the iodide coloration faded, and the reaction mixture was heated to reflux using an oil bath. The rest of ether solution (3.6 mL) was added slowly over 15 to 20 minutes. The reaction mixture was heated at 35° C. to 40° C. for another 1 hour, cooled to room temperature. To this Grignard reagent solution 2 was added 2-methyloxirane 3 (1.7 mL, 24.2 mmol) and copper iodide (35 mg, 0.18 mmol). The resultant mixture was stirred at 0° C. and brought to room temperature over 16 hours while stirring. The reaction mixture was cooled to 0° C. to 5° C., quenched with saturated ammonium chloride aqueous solution (20 mL), and extracted with EtOAc (20 mL×2). The combined organic solution was washed with brine, dried over sodium sulphate, filtered, and concentrated under vacuum to get crude oil product. The crude oil was purified by flash silica gel chromatography eluting with 10% EtOAc in hexanes to obtain expected product 1-(benzo[b]thiophen-6-yl) propan-2-ol 4 (0.34 g, 89% yield) as pale-yellow oil. $^1$H NMR (600 MHz, $CDCl_3$): δ 7.69 (d, J=7.8 Hz, 1H), 7.65 (d, J=0.6 Hz, 1H), 7.32 (d, J=5.4 Hz, 1H), 7.22 (dd, J=0.6 and 5.4 Hz, 1H), 7.14 (dd, J=1.8 and 7.8 Hz, 1H), 3.99-4.02 (m, 1H), 2.84 (dd, J=4.8 and 13.2 Hz, 1H), 2.74 (dd, J=7.8 and 13.2 Hz, 1H), 1.20 (d, J=6.0 Hz, 3H).

As described in Scheme 3, the present inventors demonstrated the synthesis of precursor compound 1-(benzo[b] thiophen-6-yl) propan-2-one (5).

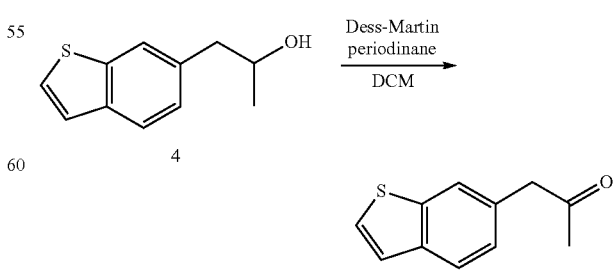

As described in Scheme 3, the present inventors demonstrated the synthesis of precursor compound 1-(benzo[b] thiophen-6-yl) propan-2-ol (4).

In this embodiment, to a solution of 4 (0.34 g, 1.76 mmol) in dichloromethane (DCM) (10 mL) was added Dess-Martin Periodinane solid (1.0 g, 2.35 mmol) in portions. After stirring at room temperature for 1 hour, the reaction mixture was analyzed by TLC to check the progress of the reaction and confirm the completion of the reaction The reaction mixture was quenched with saturated sodium bicarbonate aqueous solution (10 mL), extracted with DCM (10 mL×2). The combined organic solution was washed with brine, dried over $Na_2SO_4$, filtered, and concentrated under vacuum to give a crude oil. The crude oil was purified by flash silica gel chromatography eluting with 10% EtOAc in hexanes to get expected product 1-(benzo[b]thiophen-6-yl) propan-2-one 5 (0.25 g, 74% yield) as pale-yellow solid. $^1$H NMR (600 MHz, $CDCl_3$): δ 7.80 (d, J=7.8 Hz, 1H), 7.75 (d, J=0.6 Hz, 1H), 7.44 (d, J=5.4 Hz, 1H), 7.33 (dd, J=0.6 and 5.4 Hz, 1H), 7.22 (dd, J=1.2 and 7.8 Hz, 1H), 3.84 (s, 2H), 2.20 (s, 3H).

As described in Scheme 3, the present inventors demonstrated the synthesis of 1-(benzo[b]thiophen-6-yl)-N-methylpropan-2-amine hydrochloride (MY300 or Formula II).

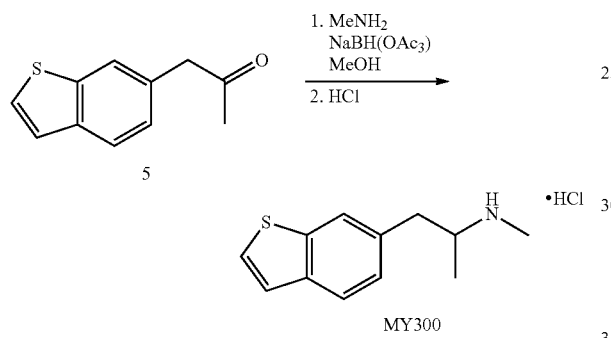

MY300

In this embodiment, to a solution of 5 (0.25 g, 1.31 mmol) in methanol (20 mL) at 0° C. to 5° C. was added a solution of 33% (wt.) methylamine in ethanol (0.8 mL, 6.4 mmol) followed by sodium triacetoxy-borohydride (0.8 g, 3.77 mmol). The resultant mixture was stirred at 0° C. to 5° C. for 2 hours, second portion of 33% (wt.) methylamine in ethanol (5 mL, 4.0 mmol) and $NaBH(OAc)_3$ (0.5 g, 2.35 mmol) were added. The reaction mixture was stirred at 0° C. to room temperature for 16 hours. The reaction mixture was diluted with water (10 mL), concentrated under vacuum to remove organic solvent. The residue was diluted with sat. $NaHCO_3$ aqueous (20 mL), extracted with DCM (20 mL×2). The combined DCM layer was washed with brine (10 mL), dried over $Na_2SO_4$, filtered and concentrated under vacuum to get crude oil. The crude oil was purified by flash silica gel chromatography eluting with 5% to 10% (10% concentrated $NH_4OH$ aqueous/90% MeOH) in DCM to afford expected product 1-(benzo[b]thiophen-6-yl)-N-methylpropan-2-amine free base (0.22 g) as pale-yellow solid. To a stirred solution of 1-(benzo[b]thiophen-6-yl)-N-methylpropan-2-amine free base (0.22 g) in EtOAc (5 mL) was added a solution of 1 M HCl in $Et_2O$ (1.7 mL, 1.7 mmol) slowly. The suspension formed was stirred at room temperature for 2 hours, filtered, washed with EtOAc (5 mL×3) and hexanes (10 mL). The filtrate cake was dried under vacuum to afford expected product 1-(benzo[b]thiophen-6-yl)-N-methylpropan-2-amine hydrochloride MY300 (0.23 g, 72% yield) as off-white solid. mp: 205° C. to 207° C. $^1$H NMR (600 MHz, $D_2O$): δ 7.86 (d, J=8.4 Hz, 1H), 7.84 (s, 1H), 7.56 (dt, J=0.6 and 6.0 Hz, 1H), 7.38 (d, J=5.4 Hz, 1H), 7.27 (d, J=7.8 Hz, 1H), 3.54 (dd, J=6.6 and 13.2 Hz, 1H), 3.15 (dd, J=6.0 and 13.2 Hz, 1H), 2.97 (dd, J=7.8 and 13.8 Hz, 1H), 2.66 (s, 3H), 1.24 (d, J=6.6 Hz, 3H). $^{13}$C NMR (150 MHz, $D_2O$): δ 140.0, 138.7, 131.9, 127.4, 125.8, 124.1, 123.7, 123.2, 56.6, 38.7, 29.9, 14.8. LCMS m/z=206 $[M+1]^+$ Example 6: Step-Wise Synthesis of 1-(benzo[b]thiophen-5-yl)-N-methylpropan-2-amine As shown in Scheme 4 below, the present invention provides for the step-wise synthesis of the compound according to MY400 (Formula IV):

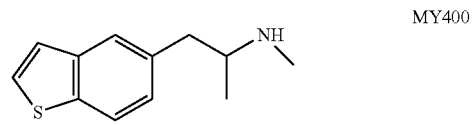

according to the following scheme:

Scheme 4

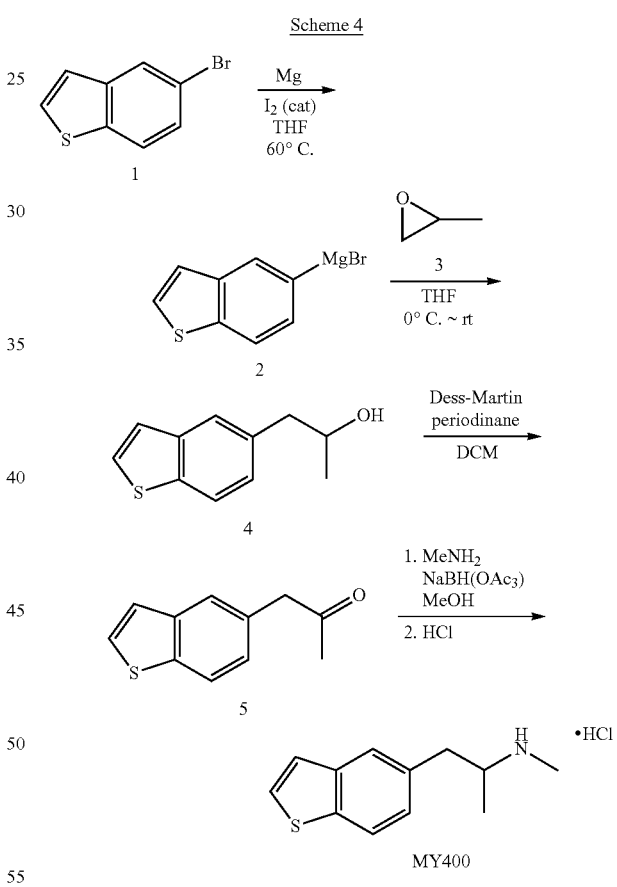

As described in Scheme 4, the present inventors demonstrated the synthesis of precursor compound 1-(benzo[b]thiophen-5-yl) propan-2-ol (4).

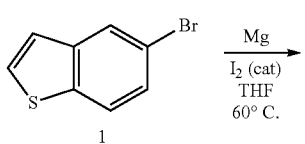

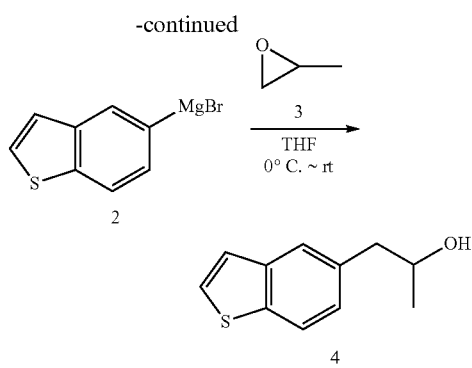

In this embodiment, to a pre-dried 3-neck flask equipped with a condenser, additional funnel and thermometer under nitrogen was charged magnesium turnings (0.1 g, 4.1 mmol), iodine (12 mg, 0.047 mmol) and tetrahydrofuran (5 mL, anhydrous). The reaction mixture was stirred and heated to 50° C. to 55° C. using a oil bath, then 0.5 mL of solution of 5-bromobenzo[b]thiophene 1 (0.5 g, 2.34 mmol in anhydrous THE 5 mL) was added. After a few minutes the iodide coloration faded, and rest of solution (4.5 mL) was added slowly over 15 to 20 minutes. The reaction mixture was heated at 50° C. to 60° C. for another 2 hours, cooled to room temperature. To this Grignard reagent solution 2 was added 2-methyloxirane 3 (0.4 mL, 5.7 mmol) and copper iodide (25 mg, 0.13 mmol). The resultant mixture was stirred at 0° C. and brought to room temperature over 16 hours while stirring. The reaction mixture was cooled to 0° C. to 5° C., quenched with saturated ammonium chloride aqueous solution. (20 mL) and extracted with EtOAc (20 mL×2). The combined organic solution was washed with brine, dried over sodium sulphate, filtered and concentrated under vacuum to give a crude oil (0.5 g). The crude oil was purified by flash silica gel chromatography eluting with 10% EtOAc in hexanes to obtain expected product 1-(benzo[b]thiophen-5-yl) propan-2-ol 4 (0.15 g, 33% yield) as pale-yellow oil. $^1$H NMR (600 MHz, CDCl$_3$): δ 7.76 (d, J=7.8 Hz, 1H), 7.60 (d, J=1.2 Hz, 1H), 7.37 (d, J=5.4 Hz, 1H), 7.23 (dd, J=0.6 and 6.0 Hz, 1H), 7.14 (dd, J=1.8 and 7.2 Hz, 1H), 3.99-4.05 (m, 1H), 2.84 (dd, J=4.8 and 13.2 Hz, 1H), 2.72 (dd, J=7.8 and 13.2 Hz, 1H), 1.20 (d, J=6.0 Hz, 3H).

As described in Scheme 4, the present inventors demonstrated the synthesis of precursor compound 1-(benzo[b]thiophen-5-yl) propan-2-one (5).

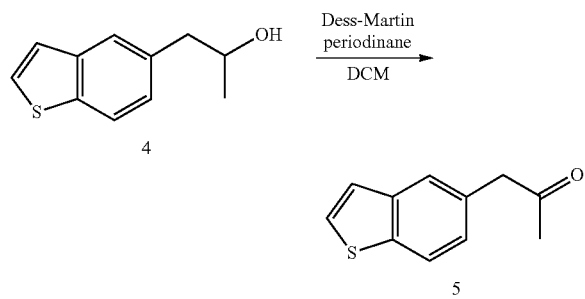

In this embodiment, to a solution of 4 (0.1 g, 0.52 mmol) in dichloromethane (4 mL) was added Dess-Martin Periodinane solid (0.27 g, 0.63 mmol) in portions. The resultant mixture was stirred at room temperature for 1 hour, TLC indicated that the trace amount of 4 remaining. Another part of Dess-Martin Periodinane (50 mg, 0.11 mmol) was added. After stirring for another 0.5 hour, the reaction mixture was analyzed by TLC to check the progress of the reaction and confirm the completion of the reaction. The reaction mixture was quenched with saturated sodium bicarbonate aqueous solution (10 mL), extracted with DCM (10 mL×2). The combined organic solution was washed with brine, dried over Na$_2$SO$_4$, filtered, and concentrated under vacuum to give a crude oil. The crude oil was purified by flash silica gel chromatography eluting with 10% EtOAc in hexanes to afford expected product 1-(benzo[b]thiophen-5-yl) propan-2-one 5 (0.09 g, 91% yield) as pale-yellow oil. $^1$H NMR (600 MHz, CDCl$_3$): δ 7.78 (d, J=8.4 Hz, 1H), 7.59 (d, J=1.2 Hz, 1H), 7.38 (d, J=5.4 Hz, 1H), 7.22 (dd, J=0.6 and 5.4 Hz, 1H), 7.11 (dd, J=1.2 and 8.4 Hz, 1H), 3.74 (s, 2H), 2.10 (s, 3H).

As described in Scheme 4, the present inventors demonstrated the synthesis of 1-(benzo[b]thiophen-5-yl)-N-methylpropan-2-amine hydrochloride (MY400).

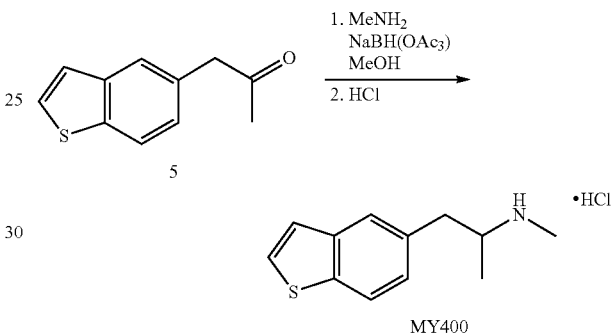

In this embodiment, to a solution of 5 (0.09 g, 0.47 mmol) in MeOH (10 mL) at 0° C. to 5° C. was added a solution of 33% (wt.) methylamine in ethanol (0.3 mL, 2.4 mmol) followed by sodium triacetoxyborohydride (0.3 g, 1.4 mmol). The resultant mixture was stirred at 0° C. to 5° C. for 2 hours, second portion of 33% (wt.) methylamine in ethanol (0.2 mL, 1.6 mmol) and NaBH(OAc)$_3$ (0.15 g, 0.7 mmol) were added. The reaction mixture was stirred at 0° C. to room temperature for 16. The reaction mixture was diluted with water (10 mL), concentrated under vacuum to remove organic solvent. The residue was diluted with sat. NaHCO$_3$ aq (20 mL), extracted with DCM (20 mL×2). The combined DCM layer was washed with brine (10 mL), dried over Na$_2$SO$_4$, filtered and concentrated under vacuum to give crude oil. The crude oil was purified by flash silica gel chromatography eluting with 5% to 10% (10% concentrated NH$_4$OH aqueous/90% MeOH) in DCM to afford expected product 1-(benzo[b]thiophen-5-yl)-N-methylpropan-2-amine free base (0.084 g, 87% yield) as pale-yellow solid.

To a stirred solution of 1-(benzo[b]thiophen-5-yl)-N-methylpropan-2-amine free base (0.113 g, 0.55 mmol) in EtOAc (4 mL) was added a solution of 1 M HCl in Et$_2$O (0.8 mL, 0.8 mmol) slowly. The suspension formed was stirred at room temperature for 2 hours, filtered, washed with EtOAc (3 mL×3) and hexanes (5 mL). The filtrate cake was dried under vacuum to afford expected product 1-(benzo[b]thiophen-5-yl)-N-methylpropan-2-amine hydrochloride MY400 (0.116 g, 87% yield) as off-white solid. mp: 202° C.-204° C. $^1$H NMR (600 MHz, D$_2$O): d 7.94 (d, J=8.4 Hz, 1H), 7.77 (s, 1H), 7.61 (d, J=5.4 Hz, 1H), 7.38 (d, J=5.4 Hz, 1H), 7.26 (d, J=8.4 Hz, 1H), 3.54 (dd, J=6.6 and 13.8 Hz, 1H), 3.15 (dd, J=6.0 and 13.8 Hz, 1H), 2.97 (dd, J=7.8 and 13.8 Hz, 1H), 2.66 (s, 3H), 1.24 (d, J=6.6 Hz, 3H). $^{13}$C NMR (150 MHz, D$_2$O): d 140.0, 138.4, 131.9, 128.1, 125.6, 124.3, 123.7, 123.1, 56.5, 38.6, 29.9, 14.8. LCMS m/z=206 [M+1]$^+$ Example 7. Synthesis of MDMA As shown in Scheme 5 below, the present invention provides for the step-wise synthesis of MDMA:

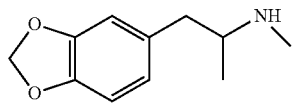
MDMA according to the following scheme:

Scheme 5

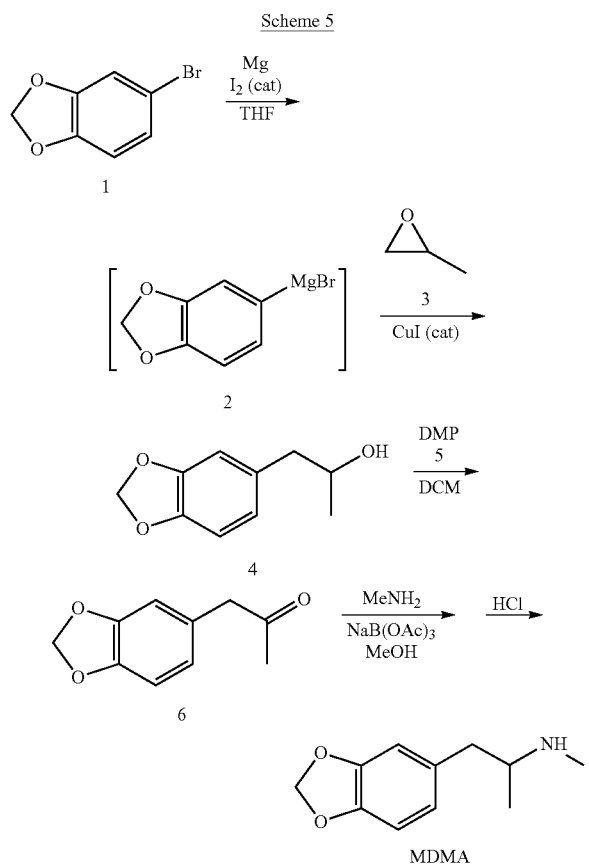
MDMA

As described in Scheme 5, the present inventors demonstrated the synthesis of the MDMA precursor compound 1-(benzo[d][1,3] dioxol-5-yl)propan-2-ol (4).

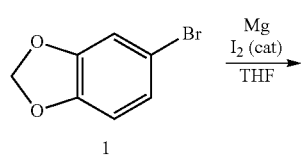

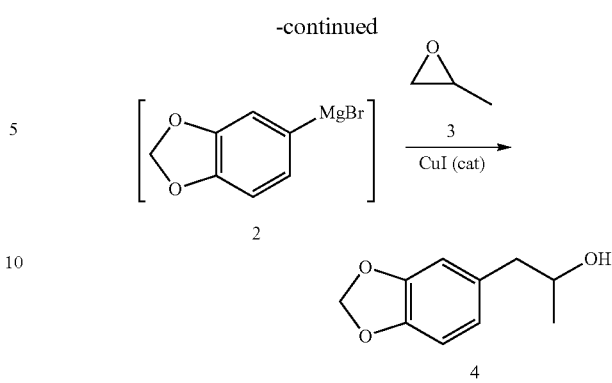

In this embodiment, to a pre-dried 3-neck 500 mL round bottom flask equipped with a condenser, additional funnel and thermometer under nitrogen was charged magnesium turnings (4.53 g, 186.5 mmol, 1.5 eq.), iodine (I$_2$) (0.1 g, 0.39 mmol, 0.003 eq) and tetrahydrofuran (THF). The solution of 4-bromo-1,2-(methylenedioxy) benzene 1 (25.0 g, 124.3 mmol, 1 eq) in THF (100 mL) was added via the additional funnel. The reaction mixture was heated at 60° C. to 70° C. for 1 hour, cooled to room temperature. To the Grignard reagent solution 2 was added 2-methyloxirane 3 (13.1 mL, 186.5 mmol, 1.5 eq), copper iodide (CuI) (1.18 g, 6.22 mmol, 0.05 eq) and anhydrous THE (100 mL) at 0° C. to 5° C. The resultant mixture was stirred at 0° C. and brought to room temperature over 16 hours while stirring. The reaction mixture was cooled to 0° C. to 5° C., quenched with a cold solution of acetic acid (AcOH, 21.3 mL, 372.9 mmol, 3.0 eq) in water (150 mL) slowly over a period of 20 to 30 minutes while keeping temperature below 25° C. The reaction mixture was diluted with ethyl acetate (EtOAc) (200 mL), sodium chloride (NaCl) solid (50 g) was added and stirred for another 20 to 30 minutes, and the layers were separated. The aqueous layer was extracted EtOAc. The combined organic layer was washed with saturated sodium bicarbonate (NaHCO$_3$) aqueous solution, brine, dried over sodium sulphate (Na$_2$SO$_4$), filtered, and concentrated under vacuum to afford crude oil product 1-(benzo[d][1,3] dioxol-5-yl)propan-2-ol 4 (22.4 g, quantitative yield) which was used in the next step without further purification. $^1$H NMR (600 MHz, CDCl$_3$): δ 6.78 (d, J=8.4 Hz, 1H), 6.73 (s, 1H), 6.68 (m, 1H), 5.96 (s, 2H), 3.98 (m, 1H), 2.73 (m, 1H), 2.61 (m, 1H), 1.32 (d, J=6.6 Hz, 3H).

As described in Scheme 5, the present inventors further demonstrated the synthesis of the MDMA precursor compound Synthesis of 1-(benzo[d][1,3] dioxol-5-yl)propan-2-one (6).

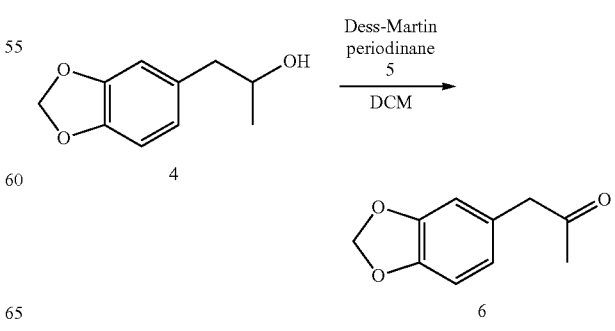

In this embodiment, to a 3-neck 500 mL round bottom flask equipped with mechanical stirrer and thermometer was charged 1-(benzo[d][1,3] dioxol-5-yl)propan-2-ol 4 (22.4 g, 124.3 mmol, 1 eq) and dichloromethane (DCM) (224 mL, 10 volume). The resultant solution was stirred and cooled to 0° C. to 5° C., and solid Dess-Martin Periodinane (DMP) (55.4 g, 130.5 mmol, 1.05 eq) was added in portions. After the DMP was added completely, the resultant solution was stirred at 0° C. to 5° C. for 1 hour and brought to room temperature over a period 2 hours while stirring, and precipitation formed. The reaction mixture was analyzed by TLC to check the progress of the reaction and confirm the completion of the reaction. The reaction mixture was then cooled to 0° C. to 5° C. and quenched slowly with saturated sodium bicarbonate (NaHCO$_3$) aqueous solution (400 mL) to pH 8, and sodium thiosulfate (Na$_2$S$_2$O$_3$) (10 g) was added to quench excess DMP. The resultant suspension was stirred at room temperature for 1 hour, filtered through celite, and rinsed with DCM. The two-layer filtrate was separated, and the aq layer was extracted with DCM. The combined DCM layer was dried over Na$_2$SO$_4$, filtered, and concentrated under vacuum to give a brown crude oil (25.8 g). The crude oil was stirred in hexanes at 60° C. for 30 minutes and the clear hexanes solution was decanted. The clear solution was concentrated under vacuum to afford 1-(benzo[d][1,3] dioxol-5-yl)propan-2-one 6 (18.7 g, 84% yield) as yellow oil. $^1$H NMR (600 MHz, CDCl$_3$): δ 6.70 (d, J=7.8 Hz, 1H), 6.60 (s, 1H), 6.57 (m, 1H), 5.87 (s, 2H), 3.52 (s, 2H), 2.07 (s, 3H).

As described in Scheme 5, the present inventors further demonstrated the synthesis of the 1-(benzo[d][1,3] dioxol-5-yl)-N-methylpropan-2-amine hydrochloride (MDMA), shown herein as a pharmaceutically acceptable salt:

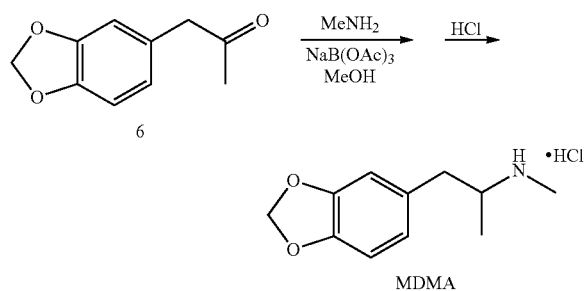

In this embodiment, to a 3-neck 1 L round bottom as equipped with mechanical stirrer and thermometer was charged 1-(benzo[d][1,3] dioxol-5-yl)propan-2-one 6 (18.7 g, 104.9 mmol, 1 eq) and methanol (MeOH) (374 mL, 20 volume eq). The resultant mixture was stirred and cooled to 0° C. to 5° C., a solution of 33 wt % methylamine (MeNH$_2$) in ethanol (EtOH) (39.2 mL, 315 mmol, 3 eq) was added slowly, followed by solid by sodium triacetoxy-borohydride (NaBH(OAc)$_3$) (44.5 g, 210 mmol, 2 eq) in portions over a period of 15 to 20 minutes. The resultant mixture was stirred at 0° C. to 5° C. for 2 hours, second portion of 33 wt % MeNH$_2$ in EtOH (13.1 mL, 105 mmol, 1 eq) and NaBH (OAc)$_3$ (22.3 g, 105 mmol, 1 eq) was added slowly. The reaction mixture was stirred at 0° C. to room temperature for 16 hours and analyzed by TLC to check the progress of the reaction and confirm the completion of the reaction. The reaction mixture was diluted with water (250 mL), stirred at room temperature for another 0.5 hour, and concentrated under vacuum to remove organic solvent. The residue was stirred and diluted with water (250 mL), cooled to 0° C. to 5° C., and concentrated HCl aqueous (75 mL, 0.9 mol) was added slowly via an additional funnel over a period of 30 to 40 minutes (pH 1 to 2). The reaction mixture was extracted with EtOAc. The aqueous layer was diluted with DCM (200 mL), stirred, and cooled to 0° C. to 5° C., and a pre-cooled solution of sodium hydroxide (NaOH) (40 g, 1 mol) in water (120 mL) was added slowly via an additional funnel (pH 10 to 11). The layers were separated, and the aqueous layer was extracted with DCM. The combined DCM layer was washed with water, dried over Na$_2$SO$_4$, filtered, and concentrated under vacuum to give MDMA free base as brown oil (15 g). The crude oil was dissolved in EtOAc (150 mL), cooled to 5° C. to 10° C., and a solution of 1 M HCl in diethyl ether (Et$_2$O) (100 mL, 100 mmol) was added slowly over a period of 15 to 20 minutes via an additional funnel. The resultant suspension was stirred at room temperature for 16 hours, filtered, washed with EtOAc, dried in air to give crude MDMA HCl salt (16.7 g) as a brown solid, which was recrystalized in EtOH to afford MDMA HCl salt (10.0 g, 41% yield) as off-white solid. mp: 148° C. to 150° C. $^1$H NMR (600 MHz, D$_2$O): d 6.68 (d, J=7.8 Hz, 1H), 6.78 (d, J=1.2 Hz, 1H), 7.72 (dd, J=1.2 and 7.8 Hz, 1H), 5.90 (s, 2H), 3.42 (m, 1H), 2.91 (dd, J=6.6 and 14.4 Hz, 1H), 2.77 (dd, J=6.6 and 14.4 Hz, 1H), 2.63 (s, 3H), 1.21 (d, J=6.6 Hz, 3H). $^{13}$C NMR (150 MHz, D$_2$O): d 147.5, 146.3, 129.4, 122.7, 109.6, 108.7, 101.1, 56.4, 38.4, 29.8, 14.7. LCMS m/z=194 [M+1]$^+$ Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Bond designations showing a {bond, denotes different enantiomeric forms, which are specifically claimed. Specifically, where a chemical bond is shown as a "{" the claims and disclosure specifically claims racemic mixtures, as well as the isolated and mixtures of enantiomeric forms of the compound. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of this invention. Such compounds are useful, for example, as analytical tools, as probes in biological assays, or as therapeutic agents in accordance with the present invention. The term "stereoisomer" refers to a molecule that is an enantiomer, diastereomer or geometric isomer of a molecule. Stereoisomers, unlike structural isomers, do not differ with respect to the number and types of atoms in the molecule's structure but with respect to the spatial arrangement of the molecule's atoms. Examples of stereoisomers include the (+) and (−) forms of optically active molecules.

As used herein the term "duration of action" means the time period after administration of one or more of the compounds of the invention during which a physiological, psychological therapeutic response is present in a subject, and preferably a human subject. Generally, the duration of action of one or more of the compounds of the invention is dependent on multiple factors, including subject, does and pharmacokinetic actions within the body as well as metabolic clearance time.

As used herein the term "methylenedioxy" means a functional group with the structural formula —O—CH$_2$—O—, which is connected to the molecule via two chemical bonds through oxygen.

As used herein the term "benzoxathiole" means a bicyclic heterocycle consisting of a benzene ring fused to an oxathiole molecule. An exemplary benzoxathiole, includes 1,3 benzoxathiole having a formula according to:

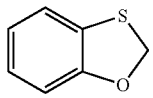

As used herein the term "benzthiophene" means a bicyclic aromatic heterocycle in which a benzene ring is fused to a thiophene molecule. An exemplary benzoxathiole, includes 1, benzthiophene having the general formulas according to:

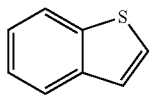

As used herein the term "oxygenase" refers to any of the class of enzymes that catalyze the incorporation of molecular oxygen into its substrate. In one embodiment, an oxygenase may include the monooxygenase cytochrome P450, and preferably a human cytochrome P450.

As used herein the term "peroxidase"% means an enzyme that oxidizes a substrate by a peroxidase type mechanism, utilizing an enzyme cofactor of the form ROOH or its equivalent.

As used herein the singular forms "a", "an", and "the" include plural referents unless the context clearly dictates otherwise. Thus, for example, reference to "a compound" includes a plurality of such compounds, and reference to "the method" includes reference to one or more methods, method steps, and equivalents thereof known to those skilled in the art, and so forth. Similarly, the word "or" is intended to include "and" unless the context clearly indicates otherwise. Hence "comprising A or B" means including A, or B, or A and B. Furthermore, the use of the term "including", as well as other related forms, such as "includes" and "included", is not limiting.

The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or ±a range of up to 20%, up to 15%, up to 10%, up to 5%, or up to 4%, 3%, 2%, or 1% compared to the specifically recited value.

The term "compound," "active compound," or "composition," or "compound of the invention" includes all solvates, complexes, polymorphs, radiolabeled derivatives, tautomers, stereoisomers, and optical isomers of the novel MDMA analog compounds generally described herein, and salts thereof, unless otherwise specified. Notably, if the compound is anionic, or has a functional group which may be anionic (e.g., —COH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$^{2+}$, NHR$_3^+$, NR$_4$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic or has a functional group which may be cationic (e.g., NH$_2$ may be NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc. It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, "Protective Groups in Organic Synthesis" (T. Green and P. Wuts; 3rd Edition; John Wiley and Sons, 1999). For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, NH-Cbz); as a t-butoxy amide (—NHCO—OC(CH$_3$)$_3$, NH-Boc); a 2-biphenyl-2-propoxy amide (—NHCO—OC(CH$_3$)$_2$C$_6$H$_4$C$_6$H$_5$, NH-Bpoc), as a 9-fluorenylmethoxy amide (NH-Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH—Psec); or, in suitable cases, as an N-oxide (>NO). For example, a carboxylic acid group may be protected as an ester for example, as: a C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(═O)CH$_3$).

It may be convenient or desirable to prepare, purify, and/or handle the active compound in the form of a prodrug. The term "prodrug", as used herein, pertains to a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(═O) OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required. Examples of such metabolically labile esters include, but are not limited to, those wherein R is C$_{1-20}$ alkyl (e.g. -Me, -Et); CI-7 aminoalkyl (e.g. aminoethyl; 2-(N,N-diethylamino)ethyl; 2-(4-morpholino)ethyl); and acyloxy-C$_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl) carbonyloxymethyl; and 1-(4-tetrahydropyranyl) carbonyloxyethyl).

Further suitable prodrug forms include phosphonate and glycolate salts. In particular, hydroxy groups (—OH), can be made into phosphonate prodrugs by reaction with chlorodibenzylphosphite, followed by hydrogenation, to form a phosphonate group —O—P(═O)(OH)$_2$. Such a group can be cleaved by phosphatase enzymes during metabolism to yield the active drug with the hydroxy group.

Also, some prodrugs are activated enzymatically to yield the active compound, or a compound which, upon further chemical reaction, yields the active compound. For example, the prodrug may be a sugar derivative or other glycoside conjugate or may be an amino acid ester derivative.

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-group s/substituents include alkyl groups, hydroxyl groups, alkoxy groups, acyloxy groups, mercapto groups, and aryl groups.

Aromatic groups containing one or more heteroatoms (typically N, O or S) as ring members can be referred to as heteroaryl or heteroaromatic groups. Typical heteroaromatic groups include monocyclic C5-C6 aromatic groups such as pyridyl, pyrimidyl, pyrazinyl, thienyl, furanyl, pyrrolyl, pyrazolyl, thiazolyl, oxazolyl, isothiazolyl, isoxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, pyrazolopyrimidyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms.

As also used herein, the terms "heterocycle", "cycloheteroalkyl", and "heterocyclic moieties" are used interchangeably herein and refer to any compound in which a plurality of atoms form a ring via a plurality of covalent bonds, wherein the ring includes at least one atom other than a carbon atom as a ring member. Particularly contemplated heterocyclic rings include 5- and 6-membered rings with nitrogen, sulfur, or oxygen as the non-carbon atom (e.g., imidazole, pyrrole, triazole, dihydropyrimidine, indole, pyridine, thiazole, tetrazole etc.). Typically, these rings contain 0-1 oxygen or sulfur atoms, at least one and typically 2-3 carbon atoms, and up to four nitrogen atoms as ring members. Further contemplated heterocycles may be fused (i.e., covalently bound with two atoms on the first heterocyclic ring) to one or two carbocyclic rings or heterocycles and are thus termed "fused heterocycle" or "fused heterocyclic ring" or "fused heterocyclic moieties" as used herein. Where the ring is aromatic, these can be referred to herein as 'heteroaryl' or heteroaromatic groups.

Heterocyclic groups that are not aromatic can be substituted with groups suitable for alkyl group substituents, as set forth above.

The term "aliphatic" as applied to cyclic groups refers to ring structures in which any double bonds that are present in the ring are not conjugated around the entire ring structure.

The term "aromatic" as applied to cyclic groups refers to ring structures which contain double bonds that are conjugated around the entire ring structure, possibly through a heteroatom such as an oxygen atom or a nitrogen atom. Aryl groups, pyridyl groups and furan groups are examples of aromatic groups. The conjugated system of an aromatic group contains a characteristic number of electrons, for example, 6 or 10 electrons that occupy the electronic orbitals making up the conjugated system, which are typically unhybridized p-orbitals.

The term "substituted" as used herein refers to a replacement of a hydrogen atom of the unsubstituted group with a functional group, and particularly contemplated functional groups include nucleophilic groups (e.g., —NH$_2$, —OH, —SH, —CN, etc.), electrophilic groups (e.g., C(O)OR, C(X)OH, etc.), polar groups (e.g., OH), non-polar groups (e.g., heterocycle, aryl, alkyl, alkenyl, alkynyl, etc.), ionic groups (e.g., —NH$_3$+), and halogens (e.g., —F, —Cl), NHCOR, NHCONH2, OCH2COOH, OCH2CONH2, OCH2CONHR, NHCH2COOH, NHCH2CONH2, NHSO2R, OCH2-heterocycles, PO3H, SO₃H, amino acids, and all chemically reasonable combinations thereof. Moreover, the term "substituted" also includes multiple degrees of substitution, and where multiple substituents are disclosed or claimed, the substituted compound can be independently substituted by one or more of the disclosed or claimed substituent moieties.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, compounds arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

The term "modulation" as used herein in the context of serotonin, or other receptor binding, refers to a change in activation state as compared to the absence of a compound of the invention, or a patent compound of one or more of the compounds of the invention.

The term "beneficial" as used herein in the context of treating a condition, refers to extended relieve of symptoms (duration) and/or a more significant reduction of symptoms (magnitude).

As used herein, a "therapeutically effective amount" for treating or preventing one or more symptoms of a disease or condition, which may preferably include, but not be limited to: for schizophrenia, a therapeutically effective amount is an amount which causes a significant reduction in psychopathology as determined by clinical improvement; for depression, a therapeutically effective amount is an amount that leads to stabilization and remission of symptoms as measured by the Patient Health Questionnaire-9; for OCD, a therapeutically effective amount is an amount that leads to stabilization and remission of symptoms as measured by the Yale-Brown Obsessive Compulsive Scale; for ADHD, a therapeutically effective amount is an amount that leads to stabilization and remission of symptoms as measured by either the ADHD Rating Scale V or ADHD Self-Report Scale; for eating disorders, a therapeutically effective amount is an amount that leads to stabilization and remission of symptoms as measured by the Eating Disorder Examination Questionnaire; for autism spectrum disorders a therapeutically effective amount is an amount that leads to stabilization and remission of symptoms as measured by physicians' assessment; for PTSD a therapeutically effective amount is an amount that leads to stabilization and remission of symptoms as measured by the Clinician-Administered PTSD Scale for DSM-5; for anxiety, a therapeutically effective amount is an amount that leads to stabilization and remission of symptoms as measured by the General Anxiety Disorder-7; for addiction, a therapeutically effective amount is an amount that leads to stabilization and remission of symptoms as measured by physicians' assessment; for cluster headaches, a therapeutically effective amount is an amount that leads to stabilization and remission of symptoms as measured by the Cluster Headache Severity Scale (CHSS); for dementia, a therapeutically effective amount is an amount that leads to stabilization and remission of symptoms as measured by the Dementia Rating Scale (DRS); for Alzheimer's disease, a therapeutically effective amount is an amount that leads to stabilization and remission of symptoms as measured by the Alzheimer's Disease Assessment Scale-Cognitive Subscale (ADAS-Cog); for paralysis, a therapeutically effective amount is an amount that leads to stabilization and remission of symptoms as measured by physicians' assessment.

The term "treatment" or "treating", as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition). The pharmaceutical acceptable carrier may comprise any conventional pharmaceutical carrier or excipient. The choice of carrier and/or excipient will to a large extent depend on factors such as the particular mode of administration, the effect of the carrier or excipient on solubility and stability, and the nature of the dosage form.

Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus, for oral administration, tablets containing various excipients, such as citric acid may be employed together with various disintegrants such as starch, alginic acid and certain complex silicates and with binding agents such as sucrose, gelatin and acacia. Examples, without limitation, of excipients include calcium carbonate, calcium phosphate, various sugars and types of starch, cellulose derivatives, gelatin, vegetable oils and polyethylene glycols. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The term "pharmaceutically acceptable salt" means a salt which is acceptable for administration to a patient, such as a mammal, such as human (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt. For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned above are meant to comprise the therapeutically active non-toxic acid and base addition salt forms which the compounds can form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic, and like acids. Conversely, these salt forms can be converted into the free base form by treatment with an appropriate base. The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g., the lithium, sodium, potassium, magnesium, calcium salts and the like, salts with organic bases, e.g., the benzathine, N-methyl-D-glucamine, hydrabamine salts, and salts with amino acids such as, for example, arginine, lysine, and the like.

What is claimed is:

1. A MDMA analog compound according to Formula (V) comprising:
wherein:

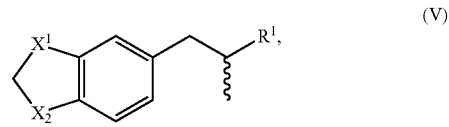

$X^1$ is S;
$X^2$ is O;
$R^1$ is $NR^2R^3$;
$R^2$ is H or $CH_3$;
$R^3$ is $CH_3$;
or a pharmaceutically acceptable salt thereof.

2. The compound of claim 1, wherein the compound is the compound of Formula I:

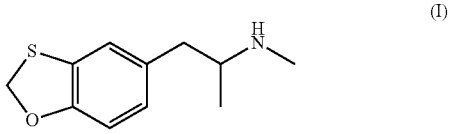

3. A pharmaceutical composition comprising a therapeutically effective amount of the compound of claim 1, and at least one pharmaceutically acceptable carrier.

4. The pharmaceutical composition of claim 3, further comprising at least one further therapeutic agent selected from: a tryptamine compound, an entactogen compound, or a combination of the same.

5. A pharmaceutical composition comprising a therapeutically effective amount of the compound of claim 2, and at least one pharmaceutically acceptable carrier.

6. The pharmaceutical composition of claim 5, further comprising at least one further therapeutic agent selected from: a tryptamine compound, an entactogen compound, or a combination of the same.

* * * * *